(12) United States Patent
Oestergaard et al.

(10) Patent No.: US 7,608,444 B2
(45) Date of Patent: *Oct. 27, 2009

(54) USE OF ACID STABLE PROTEASE IN ANIMAL FEED

(75) Inventors: Peter Rahbek Oestergaard, Virum (DK); Carsten Sjoeholm, Alleroed (DK); Anna-Marie Kluenter, Loerrach (DE)

(73) Assignee: DSM IP Assets B.V. (NL)

( * ) Notice: Subject to any disclaimer, the term of this patent is extended or adjusted under 35 U.S.C. 154(b) by 208 days.

This patent is subject to a terminal disclaimer.

(21) Appl. No.: 11/074,491

(22) Filed: Mar. 8, 2005

(65) Prior Publication Data

US 2005/0148060 A1   Jul. 7, 2005

Related U.S. Application Data

(63) Continuation of application No. 09/779,334, filed on Feb. 8, 2001, now Pat. No. 6,960,462.

(60) Provisional application No. 60/183,133, filed on Feb. 17, 2000.

(30) Foreign Application Priority Data

Feb. 8, 2000 (DK) ............................... 2000 00200

(51) Int. Cl.
   *C12N 9/50* (2006.01)
(52) U.S. Cl. ..................................... 435/219
(58) Field of Classification Search ............. None
   See application file for complete search history.

(56) References Cited

U.S. PATENT DOCUMENTS

| | | | |
|---|---|---|---|
| 3,652,399 A | 3/1972 | Isono et al. |
| 3,674,643 A | 7/1972 | Aunstrup et al. |
| 3,683,069 A | 8/1972 | Hooreman et al. |
| 3,723,250 A | 3/1973 | Aunstrup et al. |
| 3,823,072 A | 7/1974 | Hooreman et al. |
| 3,868,448 A | 2/1975 | Hahn et al. |
| 3,966,971 A | 6/1976 | Morehouse et al. |
| 4,052,262 A | 10/1977 | Horikoshi et al. |
| 4,062,732 A | 12/1977 | Lehmann et al. |
| 4,073,884 A | 2/1978 | Hartdegen et al. |
| 4,218,437 A | 8/1980 | Hiller et al. |
| 4,225,584 A | 9/1980 | Hiller et al. |
| 4,239,750 A | 12/1980 | Hiller et al. |
| 4,429,044 A | 1/1984 | Boguslawski et al. |
| 4,473,644 A | 9/1984 | Schindler et al. |
| 4,480,037 A | 10/1984 | Ichishima et al. |
| 4,518,697 A | 5/1985 | Bartnik et al. |
| 5,047,240 A | 9/1991 | Hooreman et al. |
| 5,312,748 A | 5/1994 | Liu et al. |
| 5,597,720 A | 1/1997 | Outtrup et al. |
| 6,558,693 B1 | 5/2003 | Knap et al. |
| 6,855,548 B2 | 2/2005 | Sjoeholm et al. |
| 7,179,630 B2 | 2/2007 | Lassen et al. |
| 2006/0147499 A1 | 7/2006 | Oestergaard et al. |

FOREIGN PATENT DOCUMENTS

| | | |
|---|---|---|
| EP | 130756 | 2/1991 |
| EP | 0 897 985 | 2/1999 |
| EP | 908105 | 4/1999 |
| SU | 779383 | 11/1980 |
| WO | WO 91/10723 | 7/1991 |
| WO | WO 93/24623 | 12/1993 |
| WO | WO 95/02044 | 1/1995 |
| WO | WO 95/21540 | 8/1995 |
| WO | WO 95/28850 | 11/1995 |
| WO | WO 96/05739 | 2/1996 |
| WO | WO 98/56260 | 12/1998 |
| WO | WO 99/53038 | 10/1999 |
| WO | WO 01/58275 | 8/2001 |

OTHER PUBLICATIONS

Barrett, A.J. et al., Handbook of Proteolytic Enzymes, Academic Press, pp. 887-898 (1998).
Kaneda, M. et al., Isolation And Characterization of a Proteinase, Journal of Biochemistry, vol. 78, pp. 1287-1296 (1975).
Gill, S. et al., Calculation of Protein Extinction, Analytical Biochemistry, vol. 182, pp. 319-326 (1989).
Michalik, I. et al., Isolation and Utilization in Animal Nutrition, Ukr, Biokhim Zh, vol. 69, Part 3, pp. 28-35 (1997).
Caine, W.R. et al., Effect of Protease Treatment of Soybean Meal, Animal Feed Science and Technology, vol. 177-183 (1998).
Needleman & Wunsch, A general method applicable to the search for similarities in the amino acid, Journal of Molecular Biology, vol. 48, pp. 443-453 (1970).
Smith, et al., Measurement of Protein Using Bicinchroninic Acid, Analytical Biochemistry, vol. 150, pp. 76-85 (1985).
Van Heynigen S et al., An Alkaline Protease, European Journal of Biochemistry, vol. 48, pp. 432-437 (1972).
Van Heynigen et al., A new Alkaline Protease, Biochemical Journal, vol. 125, pp. 1159-1160 (1971).
Higgins et al., Gene, vol. 73, pp. 237-244 (1988) Clustal: A package for performing multiple sequence alignments on a microcomputer.
Refstie et al., Aquaculture, vol. 162, pp. 301-312 (1998).
Altschul et al., Nucleic Acids, vol. 25, pp. 3389-3402 (1997) Gapped BLAST and PSI-BLAST: A new generation of protein data base search programs.
Snow Brand Milk Products, Abstract of JP 02255081 (1990)Protease producing microbe - is Streptomyces nocardiapsis sp OPC. 120 growing in alkaline conditions.
Title for Refstie - Feed consumption and in conversion Atlantic salmon (Salmo salar) fed diets with fish meal, extracted soybean meal or soybean meal with reduced content of oligosaccharides, trypsin inhibitors, lectins and soy antigens.

*Primary Examiner*—Cecilia Tsang
*Assistant Examiner*—Christina Marchetti Bradley
(74) *Attorney, Agent, or Firm*—Elias Lambiris

(57) ABSTRACT

The present invention relates to acid-stable proteases of the subtilisin family, their use in animal feed, feed-additives and feed compositions containing such proteases, and methods for the treatment of vegetable proteins using such proteases.

14 Claims, 6 Drawing Sheets

USE OF ACID STABLE PROTEASE IN ANIMAL FEED

CROSS-REFERENCE TO RELATED APPLICATIONS

This application is a continuation of U.S. application Ser. No. 09/779,334 filed Feb. 8, 2001, now U.S. Pat. No. 6,960,462, which claims priority or the benefit under 35 U.S.C. 119 of Danish application no. PA 2000 00200 filed Feb. 8, 2000 and U.S. provisional application No. 60/183,133 filed Feb. 17, 2000, the contents of which are fully incorporated herein by reference.

FIELD OF THE INVENTION

The present invention relates to the use of acid-stable, serine proteases of the subtilisin family in animal feed (in vivo), and to the use of such proteases for treating vegetable proteins (in vitro).

Proteins are essential nutritional factors for animals and humans. Most livestock and many human beings get the necessary proteins from vegetable protein sources. Important vegetable protein sources are e.g., oilseed crops, legumes and cereals.

When e.g., soybean meal is included in the feed of mono-gastric animals such as pigs and poultry, a significant proportion of the soybean meal solids is not digested. For example, the apparent ileal protein digestibility in piglets and growing pigs is only around 80%.

The stomach of mono-gastric animals and many fish exhibits a strongly acidic pH. Most of the protein digestion, however, occurs in the small intestine. A need therefore exists for an acid-stable protease that can survive passage of the stomach.

BACKGROUND OF THE DESCRIPTION

The use of proteases in animal feed, or to treat vegetable proteins, is known from the following documents:

WO 95/28850 discloses inter alia an animal feed additive comprising a phytase and a proteolytic enzyme. Various proteolytic enzymes are specified at p. 7.

WO 96/05739 discloses an enzyme feed additive comprising xylanase and a protease. Suitable proteases are listed at p. 25.

WO 95/02044 discloses inter alia proteases derived from *Aspergillus aculeatus*, as well as the use in animal feed thereof.

U.S. Pat. No. 3,966,971 discloses a process of obtaining protein from a vegetable protein source by treatment with an acid phytase and optionally a proteolytic enzyme. Suitable proteases are specified in column 2.

U.S. Pat. Nos. 4,073,884, 5,047,240, 3,868,448, 3,823,072, and 3,683,069 describe protease preparations derived from various strains of *Streptomyces* and their use in animal feed.

These proteases, however, are not acid-stable and/or are not proteases of the subtilisin family.

SUMMARY OF THE INVENTION

Several proteases have now been identified which are found to be very acid-stable, and expectedly of an improved performance in animal feed. These proteases belong to the group of proteases known as subtilisins.

BRIEF DESCRIPTION OF DRAWINGS

The present invention is further illustrated by reference to the accompanying drawings, in which.

DETAILED DESCRIPTION OF THE INVENTION

Figure 1:
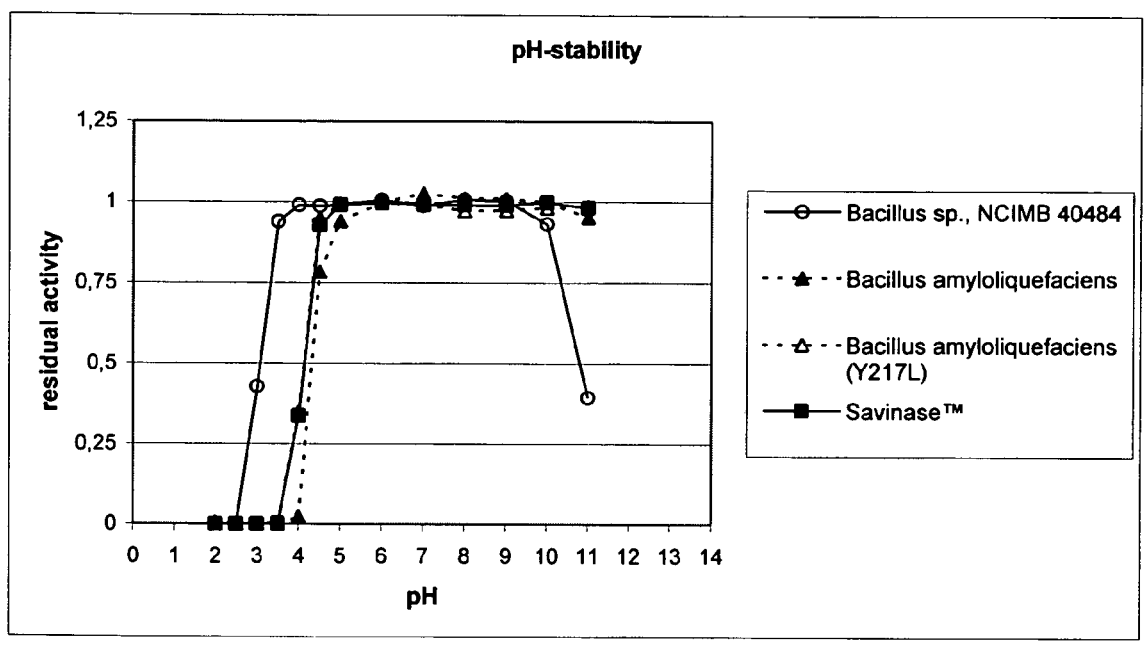
FIG. 1 shows pH-stability curves, viz. residual protease activity of four proteases (one acid-stable protease of the subtilisin family derived from *Bacillus* sp., NCIMB 40484 (PD 498), and three reference proteases (Sub. Novo, and Sub. Novo (Y217L), both derived from *Bacillus amyloliquefaciens*, and SAVINASE™) after incubation for 2 hours, at a temperature of 37° C., and at pH-values in the range of pH 2 to pH 11; the activity is relative to residual activity after a 2 hour incubation at pH 9.0, and 5° C.

The term protease as used herein is an enzyme that hydrolyzes peptide bonds (has protease activity). Proteases are also called e.g., peptidases, proteinases, peptide hydrolases, or proteolytic enzymes.

Preferred proteases for use according to the invention are of the endo-type that act internally in polypeptide chains (endopeptidases). Endopeptidases show activity on N- and C-terminally blocked peptide substrates that are relevant for the specificity of the protease in question.

Included in the above definition of protease are any enzymes belonging to the EC 3.4 enzyme group (including each of the thirteen sub-subclasses thereof) of the EC list (Enzyme Nomenclature 1992 from NC-IUBMB, 1992), as regularly supplemented and updated.

Proteases are classified on the basis of their catalytic mechanism into the following groupings: serine proteases (S), cysteine proteases (C), aspartic proteases (A), metalloproteases (M), and unknown, or as yet unclassified, proteases (U), see Handbook of Proteolytic Enzymes, A. J. Barrett, N. D. Rawlings, J. F. Woessner (eds), Academic Press (1998), in particular the general introduction part.

The term serine protease refers to serine peptidases and their clans as defined in the above Handbook. In the 1998 version of this handbook, serine peptidases and their clans are dealt with in chapters 1-175.

In a particular embodiment, serine proteases are peptidases in which the catalytic mechanism depends upon the hydroxyl group of a serine residue acting as the nucleophile that attacks the peptide bond.

The terms subtilisins or subtilisin family as used herein are intended to include all Clan SB serine proteases, in particular Family S8 thereof (Clan SB is dealt with in Chapter 93 of the above handbook). In subtilisins, the order of the catalytic triad is Asp-His-Ser. The tertiary structure includes both alphahelices and beta sheets. Clan SB includes both endopeptidases and exopeptidases. These peptidases are known from bacteria, archaea and eukaryotes; there is a single representative from a DNA virus.

For determining whether a given protease is a subtilisin or not, reference is made to the above Handbook and the principles indicated therein. Such determination can be carried out for all types of proteases, be it naturally occurring or wild-type proteases; or genetically engineered or synthetic proteases.

In the alternative, inhibition studies can be performed with SSI (the *Streptomyces* Subtilisin Inhibitor), and a subtilisin is defined as a protease with up to 10% residual activity when inhibited with a molar excess of SSI. This test may be carried out as described in Example 8. In particular embodiments of this definition, the subtilisin has up to 8%, up to 6%, or up to 5% residual activity. The expression 'up to' is considered equal to the expression 'less than or equal to'.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 5, 6, 7, 8, 9, 10, or 11. Examples of assay-temperatures are 25, 30, 35, 37, 40, 45, 50, 55, 60, 65, or 70° C.

Examples of protease substrates are casein, and pNA-substrates, such as Suc-AAPF-pNA (available e.g., from Sigma S-7388). The capital letters in this pNA-substrate refers to the one-letter amino acid code. Another example is Protazyme AK (azurine-dyed crosslinked casein prepared as tablets by Megazyme T-PRAK). For pH-activity and pH-stability studies, the pNA-substrate is preferred, whereas for temperature-activity studies, the Protazyme AK substrate is preferred.

Examples of protease assays are described in the experimental part.

There are no limitations on the origin of the protease for use according to the invention. Thus, the term protease includes not only natural or wild-type proteases, but also any mutants, variants, fragments etc. thereof exhibiting protease activity, as well as synthetic proteases, such as shuffled proteases, and consensus proteases. Such genetically engineered proteases can be prepared as is generally known in the art, e.g., by site-directed mutagenesis, by PCR (using a PCR fragment containing the desired mutation as one of the primers in the PCR reactions), or by random mutagenesis. The preparation of consensus proteins is described in e.g., EP 897985.

Examples of acid-stable proteases of the subtilisin family for use according to the invention are (i) the proteases derived from *Bacillus* sp. NCIMB 40484, *Bacillus alcalophilus*, NCIMB 10438; *Fusarium oxysporum*, IFO 4471; *Paecilomyces lilacinus*, CBS 102449, *Acremonium chrysogenum*, ATCC 48272, and *Acremonium kiliense*, ATCC 20338;

(ii) proteases of at least 70, 75, 80, 85, 90, or at least 95% amino acid identity to any of the proteases of (i);

(iii) proteases of at least 70, 75, 80, 85, 90, or at least 95% identity to any of SEQ ID NO: 1, SEQ ID NO: 2, SEQ ID NO: 3, or SEQ ID NO: 4;

(iv) proteases of at least 70, 75, 80, 85, 90, or at least 95% amino acid identity to any of SEQ ID NO: 5 (the whole sequence 1-397, or fragments 28-397 or 118-397 thereof), SEQ ID NO: 6 (the whole sequence 1-367, or fragments 70-367 or 84-367 thereof), or SEQ ID NO: 7.

For calculating percentage identity, any computer program known in the art can be used, such as GAP provided in the GCG version 8 program package (Program Manual for the Wisconsin Package, Version 8, Genetics Computer Group, 575 Science Drive, Madison, Wis., USA 53711) (Needleman, S. B. and Wunsch, C. D., (1970), Journal of Molecular Biology, 48, 443-453. Using GAP with the following settings for polypeptide sequence comparison: GAP creation penalty of 5.0 and GAP extension penalty of 0.3.

In a particular embodiment, the protease for use according to the invention is a microbial protease, the term microbial indicating that the protease is derived from, or originates from, a microorganism, or is an analogue, a fragment, a variant, a mutant, or a synthetic protease derived from a microorganism. It may be produced or expressed in the original wild-type microbial strain, in another microbial strain, or in a plant; i.e., the term covers the expression of wild-type, naturally occurring proteases, as well as expression in any host of recombinant, genetically engineered or synthetic proteases.

The term microorganism as used herein includes Archaea, bacteria, fungi, vira etc.

Examples of microorganisms are bacteria, such as bacteria of the genus *Bacillus*, e.g., *Bacillus* sp., NCIMB No.40484; *Bacillus alcalophilus*, NCIMB 10438; or mutants or variants thereof exhibiting protease activity.

Further examples of microorganisms are fungi, such as yeast or filamentous fungi, e.g., chosen from the genera *Paecilomyces*, e.g., *Paecilomyces lilacinus*, CBS 102449, *Aspergillus*, e.g., *Acremonium*, e.g., *Acremonium chrysogenum*, ATCC 48272, *Acremonium kiliense*, ATCC 20338, or *Fusarium*, e.g., *Fusarium oxysporum*, IFO 4471; or mutants or variants thereof exhibiting protease activity.

In another embodiment the protease is a plant protease. An example of a protease of plant origin is the protease from the sarcocarp of melon fruit (Kaneda et al, J. Biochem. 78, 1287-1296 (1975).

The term animal includes all animals, including human beings. Examples of animals are non-ruminants, and ruminants, such as cows, sheep and horses. In a particular embodiment, the animal is a non-ruminant animal. Non-ruminant animals include mono-gastric animals, e.g., pigs or swine (including, but not limited to, piglets, growing pigs, and sows); poultry such as turkeys and chicken (including but not limited to broiler chicks, layers); young calves; and fish (including but not limited to salmon).

The term feed or feed composition means any compound, preparation, mixture, or composition suitable for, or intended for intake by an animal.

In the use according to the invention the protease can be fed to the animal before, after, or simultaneously with the diet. The latter is preferred.

In the present context, the term acid-stable means, that the protease activity of the pure protease enzyme, in a dilution corresponding to $A_{280}=1.0$, and following incubation for 2 hours at 37° C. in the following buffer:

100 mM succinic acid, 100 mM HEPES, 100 mM CHES, 100 mM CABS, 1 mM $CaCl_2$, 150 mM KCl, 0.01% Triton® X-100, pH 3.5, is at least 40% of the reference activity, as measured using the assay described in Example 2C herein (substrate: Suc-AAPF-pNA, pH 9.0, 25° C.).

In particular embodiments of the above acid-stability definition, the protease activity is at least 45, 50, 55, 60, 65, 70, 75, 80, 85, or at least 90% of the reference activity.

The term reference activity refers to the protease activity of the same protease, following incubation in pure form, in a dilution corresponding to $A_{280}=1.0$, for 2 hours at 5° C. in the following buffer: 100 mM succinic acid, 100 mM HEPES, 100 mM CHES, 100 mM CABS, 1 mM $CaCl_2$, 150 mM KCl, 0.01% Triton®X-100, pH 9.0, wherein the activity is determined as described above.

In other words, the method of determining acid-stability comprises the following steps:

a) The protease sample to be tested (in pure form, $A_{280}=1.0$) is divided in two aliquots (I and II);

b) Aliquot I is incubated for 2 hours at 37° C. and pH 3.5;

c) Residual activity of aliquot I is measured (pH 9.0 and 25° C.);

d) Aliquot II is incubated for 2 hours at 5° C. and pH 9.0;

e) Residual activity of aliquot II is measured (pH 9.0 and 25° C.);

f) Percentage residual activity of aliquot I relative to residual activity of aliquot II is calculated.

Alternatively, in the above definition of acid-stability, the step b) buffer pH-value may be 2.0, 2.5, 3.0, 3.1, 3.2, 3.3, or 3.4.

In other alternative embodiments of the above acid-stability definition relating to the above alternative step b) buffer pH-values, the residual protease activity as compared to the reference, is at least 5, 10, 15, 20, 25, 30, 35, 40, 45, or at least 50%.

In alternative embodiments, pH values of 6.0, 6.5, 7.0, 7.5, 8.0, or 8.5 can be applied for the step d) buffer.

In the above acid-stability definition, the term $A_{280}=1.0$ means such concentration (dilution) of said pure protease which gives rise to an absorption of 1.0 at 280 nm in a 1 cm path length cuvette relative to a buffer blank.

And in the above acid-stability definition, the term pure protease refers to a sample with a $A_{280}/A_{260}$ ratio above or equal to 1.70 (see Example 2E), and which by a scan of a Coomassie-stained SDS-PAGE gel is measured to have at least 95% of its scan intensity in the band corresponding to said protease (see Example 2A). In the alternative, the $A_{280}/A_{260}$ ratio is above or equal to 1.50, 1.60, 1.65, 1.70, 1.75, 1.80, 1.85, or above or equal to 1.90.

However, for the uses according to the invention, the protease need not be that pure; it may e.g., include other enzymes, even other proteases, in which case it could be termed a protease preparation. Nevertheless, a well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

In a particular embodiment, the protease, in the form in which it is added to the feed, or when being included in a feed additive, is well-defined. Well-defined means that the protease preparation is at least 50% pure as determined by size-exclusion chromatography (see Example 12).

In other particular embodiments the protease preparation is at least 60, 70, 80, 85, 88, 90, 92, 94, or at least 95% pure as determined by this method.

In the alternative, the term well-defined means, that a fractionation of the protease preparation on an appropriate Size-exclusion column reveals only one major protease component.

The skilled worker will know how to select an appropriate size-exclusion chromatography column. He might start by fractionating the preparation on e.g., a HiLoad26/60 Superdex75pg column from Amersham Pharmacia Biotech (see Example 12). If the peaks would not be clearly separated he would try different columns (e.g., with an amended column particle size and/or column length), and/or he would amend the sample volume. By simple and common trial-and-error methods he would thereby arrive at a column with a sufficient resolution (clear separation of peaks), on the basis of which the purity calculation is performed as described in Example 12.

The protease preparation can be (a) added directly to the feed (or used directly in the treatment process of vegetable proteins), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

In one particular embodiment, the protease for use according to the invention, besides being acid-stable, also has a pH-activity optimum close to neutral.

The term pH-activity optimum close to neutral means one or more of the following: That the pH-optimum is in the interval of pH 6.0-11.0, or pH 7.0-11.0, or pH 6.0-10.0, or pH 7.0-10.0, or pH 8.0-11.0, or pH 8.0-10.0 (see Examples 2B and 7, and FIGS. 2 and 5 herein).

In another particular embodiment, the protease for use according to the invention, besides being acid-stable, is also thermostable.

The term thermostable means one or more of the following: That the temperature optimum is at least 50° C., 52° C., 54° C., 56° C., 58° C., 60° C., 62° C., 64° C., 66° C., 68° C., or at least 70° C., reference being made to Examples 2D and 7 and FIGS. 3 and 6 herein.

In a further particular embodiment, the protease for use according to the invention is capable of solubilizing vegetable proteins according to the in vitro model of Example 4 herein.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or quinoa.

Other examples of vegetable protein sources are rapeseed, and cabbage.

Soybean is a preferred vegetable protein source.

Other examples of vegetable protein sources are cereals such as barley, wheat, rye, oat, maize (corn), rice, and sorghum.

The treatment according to the invention of vegetable proteins with at least one acid-stable protease of the subtilisin family results in an increased solubilization of vegetable proteins.

The following are examples of % solubilized protein obtainable using the proteases of the invention: At least 76.8%, 77.0%, 77.2%, 77.4%, 77.6%, 77.8%, 78.0%, 78.2%, 78.4%, 78.6%, or at least 78.8%, reference being had to the in vitro model of Example 4 herein.

The term solubilization of proteins basically means bringing protein(s) into solution. Such solubilization may be due to protease-mediated release of protein from other components of the usually complex natural compositions such as feed. Solubilization can be measured as an increase in the amount of soluble proteins, by reference to a sample with no protease treatment (see Example 4 herein).

In a particular embodiment of a treatment process the protease(s) in question is affecting (or acting on, or exerting its solubilizing influence on the vegetable proteins or protein sources. To achieve this, the vegetable protein or protein source is typically suspended in a solvent, e.g., an aqueous solvent such as water, and the pH and temperature values are adjusted paying due regard to the characteristics of the enzyme in question. For example, the treatment may take place at a pH-value at which the relative activity of the actual protease is at least 50, or 60, or 70, or 80 or 90%. Likewise, for example, the treatment may take place at a temperature at which the relative activity of the actual protease is at least 50, or 60, or 70, or 80 or 90% (these relative activities being defined as in Example 2 herein). The enzymatic reaction is continued until the desired result is achieved, following which it may or may not be stopped by inactivating the enzyme, e.g., by a heat-treatment step.

In another particular embodiment of a treatment process of the invention, the protease action is sustained, meaning e.g., that the protease is added to the vegetable proteins or protein sources, but its solubilizing influence is so to speak not switched on until later when desired, once suitable solubilizing conditions are established, or once any enzyme inhibitors are inactivated, or whatever other means could have been applied to postpone the action of the enzyme.

In one embodiment the treatment is a pre-treatment of animal feed or vegetable proteins for use in animal feed, i.e., the proteins are solubilized before intake.

The term improving the nutritional value of an animal feed means improving the availability of the proteins, thereby leading to increased protein extraction, higher protein yields, and/or improved protein utilisation. The nutritional value of the feed is therefore increased, and the growth rate and/or weight gain and/or feed conversion (i.e., the weight of ingested feed relative to weight gain) of the animal is/are improved.

In particular embodiments the weight gain is at least 101%, 102%, 103%, 104%, 105%, 106%, or at least 106.6% of the control, reference being had to Example 10 herein.

In further particular embodiments the feed conversion is at most (or not more than) 99%, 98%, 97.5%, 97%, or at most 96.6%. This is equivalent to a feed conversion of up to 99%, 98%, 97.5%, 97%, or up to 96.6%. Again, reference is had to Example 10 herein, comparing with the control.

The protease can be added to the feed in any form, be it as a relatively pure protease, or in admixture with other components intended for addition to animal feed, i.e., in the form of animal feed additives, such as the so-called pre-mixes for animal feed.

Animal Feed Additives

Apart from the acid-stable protease of the subtilisin family, the animal feed additives of the invention contain at least one fat-soluble vitamin, and/or at least one water-soluble vitamin, and/or at least one trace mineral, and/or at least one macro mineral.

Further, optional, feed-additive ingredients are coloring agents, aroma compounds, stabilisers, and/or at least one other enzyme selected from amongst phytases EC 3.1.3.8 and 3.1.3.26; xylanases EC 3.2.1.8; galactanases EC 3.2.1.89; and/or beta-glucanases EC 3.2.1.4 (EC refers to Enzyme Classes according to Enzyme Nomenclature 1992 from NC-IUBMB, 1992).

In a particular embodiment these other enzymes are well-defined (as defined and exemplified above for protease preparations, inter alia, by reference to Example 12).

Usually fat- and water-soluble vitamins, as well as trace minerals form part of a so-called premix intended for addition to the feed, whereas macro minerals are usually separately added to the feed. Either of these composition types, when enriched with an acid-stable subtilisin according to the invention, is an animal feed additive of the invention.

In a particular embodiment, the animal feed additive of the invention is intended for being included (or prescribed as having to be included) in animal diets or feed at levels of 0.01-10.0%; more particularly 0.05-5.0%; or 0.2-1.0% (% meaning g additive per 100 g feed). This is so in particular for premixes.

Accordingly, the concentrations of the individual components of the animal feed additive, e.g., the premix, can be found by multiplying the final in-feed concentration of the same component by, respectively, 10-10000; 20-2000; or 100-500 (referring to the above three percentage inclusion intervals).

Guidelines for desired final concentrations, ie., in-feed-concentrations, of such individual feed and feed additive components are indicated in Table A below.

The following are non-exclusive lists of examples of these components:

Examples of fat-soluble vitamins are vitamin A, vitamin D3, vitamin E, and vitamin K, e.g., vitamin K3.

Examples of water-soluble vitamins are vitamin B12, biotin and choline, vitamin B1, vitamin B2, vitamin B6, niacin, folic acid and panthothenate, e.g., Ca-D-panthothenate.

Examples of trace minerals are manganese, zinc, iron, copper, iodine, selenium, and cobalt.

Examples of macro minerals are calcium, phosphorus and sodium.

The nutritional requirements of these components—exemplified with poultry and piglets/pigs—are listed in Table A below. Nutritional requirement means that these components should be provided in the diet in the concentrations indicated. These data are compiled from:

NRC, Nutrient requirements in swine, ninth revised edition 1988, subcommittee on swine nutrition, committee on animal nutrition, board of agriculture, national research council. National Academy Press, Washington, D.C. 1988; and NRC, Nutrient requirements of poultry, ninth revised edition 1994, subcommittee on poultry nutrition, committee on animal nutrition, board of agriculture, national research council. National Academy Press, Washington, D.C. 1994.

In the alternative, the animal feed additive of the invention comprises at least one of the individual components specified in Table A. At least one means either of, one or more of, one, or two, or three, or four and so forth up to all thirteen, or up to all fifteen individual components.

More specifically, this at least one individual component is included in the additive of the invention in such an amount as to provide an in-feed-concentration within the range indicated in column four, or column five, or column six of Table A.

As explained above, corresponding feed additive concentrations can be found by multiplying the interval limits of these ranges with 10-10000; 20-2000; or 100-500. As an example, considering which premix-content of vitamin A would correspond to the feed-content of 10-10000 IU/kg, this exercise would lead to the following intervals: 100-$10^8$ IU; or 200-$2 \times 10^7$ IU; or 1000-$5 \times 10^6$ IU per kg additive.

TABLE A

Nutrient requirements - and preferred ranges

| Nutrients provided per kg diet | Poultry | Piglets/ Pigs/Sows | Range 1 | Range 2 | Range 3 |
|---|---|---|---|---|---|
| Fat-soluble Vitamins | | | | | |
| Vitamin A/[IU] | –5000 | 1300-4000 | 10-10000 | 50-8000 | 100-6000 |
| Vitamin $D_3$/[IU] | –1100 | 150-200 | 2-3000 | 5-2000 | 10-1500 |
| Vitamin E/[IU] | –12 | 11-22 | 0.02-100 | 0.2-80 | 0.5-50 |
| Vitamin K/[mg] | 0.5-1.5 | –0.5 | 0.005-10.0 | 0.05-5.0 | 0.1-3.0 |
| Water-soluble vitamins | | | | | |
| $B_{12}$/[mg] | –0.003 | 0.005-0.02 | 0.0001-1.000 | 0.0005-0.500 | 0.001-0.100 |
| Biotin/[mg] | 0.100-0.25 | 0.05-0.08 | 0.001-10.00 | 0.005-5.00 | 0.01-1.00 |
| Choline/[mg] | 800-1600 | 300-600 | 1-10000 | 5-5000 | 10-3000 |
| Trace minerals | | | | | |
| Manganese/[mg] | –60 | 2.0-4.0 | 0.1-1000 | 0.5-500 | 1.0-100 |
| Zinc/[mg] | 40-70 | 50-100 | 1-1000 | 5-500 | 10-300 |
| Iron/[mg] | 50-80 | 40-100 | 1-1000 | 5-500 | 10-300 |
| Copper/[mg] | 6-8 | 3.0-6.0 | 0.1-1000 | 0.5-100 | 1.0-25 |
| Iodine/[mg] | –0.4 | –0.14 | 0.01-100 | 0.05-10 | 0.1-1.0 |
| Selenium/[mg] | –0.2 | 0.10-0.30 | 0.005-100 | 0.01-10.0 | 0.05-1.0 |
| Macro minerals | | | | | |
| Calcium/[g] | 8-40 | 5-9 | 0.1-200 | 0.5-150 | 1-100 |
| Phosphorus, as available phosphorus/[g] | 3-6 | 1.5-6 | 0.1-200 | 0.5-150 | 1-50 |

Animal Feed Compositions

Animal feed compositions or diets have a relatively high content of protein. According to the National Research Council (NRC) publications referred to above, poultry and pig diets can be characterized as indicated in Table B below, columns 2-3. Fish diets can be characterized as indicated in column 4 of Table B. Furthermore such fish diets usually have a crude fat content of 200-310 g/kg. These fish diet are exemplified with diets for Salmonids and designed on the basis of Aquaculture, principles and practices, ed. T. V. R. Pillay, Blackwell Scientific Publications Ltd. 1990; Fish nutrition, second edition, ed. John E. Halver, Academic Press Inc. 1989.

An animal feed composition according to the invention has a crude protein content of 50-800/kg, and furthermore comprises at least one protease as claimed herein.

Furthermore, or in the alternative (to the crude protein content indicated above), the animal feed composition of the invention has a content of metabolizable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolizable energy, crude protein, calcium, phosphorus, methionine, methionine plus cysteine, and/or lysine is within any one of ranges 2, 3, 4 or 5 in Table B below (R. 2-5).

Crude protein is calculated as nitrogen (N) multiplied by a factor 6.25, i.e., Crude protein (g/kg)=N (g/kg)×6.25 as stated in Animal Nutrition, 4th edition, Chapter 13 (Eds. P. McDonald, R. A. Edwards and J. F. D. Greenhalgh, Longman Scientific and Technical, 1988, ISBN 0-582-40903-9). The nitrogen content is determined by the Kjeldahl method (A.O.A.C., 1984, Official Methods of Analysis 14th ed., Association of Official Analytical Chemists, Washington D.C.).

Metabolizable energy can be calculated on the basis of the NRC publication Nutrient Requirements of Swine (1988) pp. 2-6, and the European Table of Energy Values for Poultry Feedstuffs, Spelderholt centre for poultry research and extension, 7361 D A Beekbergen, The Netherlands. Grafisch bedrijf Ponsen & Iooijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source as defined above.

In still further particular embodiments, the animal feed composition of the invention contains 0-80% maize; and/or 0-80% sorghum; and/or 0-70% wheat; and/or 0-70% barley; and/or 0-30% oats; and/or 0-40% soybean meal; and/or 0-10% fish meal; and/or 0-20% whey.

Animal diets can e.g., be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix. The final enzyme concentration in the diet is within the range of 0.01-200 mg enzyme protein per kg diet, for example in the range of 5-30 mg enzyme protein per kg animal diet.

Examples of animal feed compositions are shown in Example 11.

TABLE B

Range values for energy, protein and minerals in animal diets

| Nutrient | Poultry Min-Max | Piglets/ Pigs/Sows Min-Max | Fish Min-Max | R. 1 | R. 2 | R. 3 | R. 4 | R. 5 |
|---|---|---|---|---|---|---|---|---|
| Metabolizable energy, MJ/kg | 12.1-13.4 | 12.9-13.5 | 14-25 | 10-30 | 11-28 | 11-26 | 12-25 | |
| Crude protein, g/kg | 124-280 | 120-240 | 300-480 | 50-800 | 75-700 | 100-600 | 110-500 | 120-490 |
| Calcium, g/kg | 8-40 | 5-9 | 10-15 | 0.1-200 | 0.5-150 | 1-100 | 4-50 | |
| Available Phosphorus, g/kg | 2.1-6.0 | 1.5-5.5 | 3-12 | 0.1-200 | 0.5-150 | 1-100 | 1-50 | 1-25 |
| Methionine, g/kg | 3.2-5.5 | — | 12-16 | 0.1-100 | 0.5-75 | 1-50 | 1-30 | |
| Methionine plus Cysteine, g/kg | 4-9 | 2.3-6.8 | — | 0.1-150 | 0.5-125 | 1-80 | | |
| Lysine, g/kg | 2.5-11 | 6-14 | 12-22 | 0.5-50 | 0.5-40 | 1-30 | | |

In particular embodiments of the method of the invention for treating vegetable proteins, a further step of adding phytase is also included. And in further particular embodiments, in addition to the combined treatment with phytase and protease, further enzymes may also be added, wherein these enzymes are selected from the group comprising other proteases, phytases, lipolytic enzymes, and glucosidase/carbohydrase enzymes. Examples of such enzymes are indicated in WO 95/28850.

The protease should of course be applied in an effective amount, i.e., in an amount adequate for improving solubilization and/or improving nutritional value of feed. It is at present contemplated that the enzyme is administered in one or more of the following amounts (dosage ranges): 0.01-200; or 0.01-100; or 0.05-100; or 0.05-50; or 0.10-10—all these ranges being in mg protease protein per kg feed (ppm).

For determining mg protease protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg protease protein per kg feed is calculated.

The same principles apply for determining mg protease protein in feed additives.

Of course, if a sample is available of the protease used for preparing the feed additive or the feed, the specific activity is determined from this sample (no need to purify the protease from the feed composition or the additive).

Many vegetables contain anti-nutritional factors such as lectins and trypsin inhibitors. The most important anti-nutritional factors of soybean are the lectin soybean agglutinin (SBA), and the soybean trypsin inhibitor (STI).

Lectins are proteins that bind to specific carbohydrate-containing molecules with considerable specificity, and when ingested they become bound to the intestinal epithelium. This may lead to reduced viability of the epithelial cells and reduced absorption of nutrients.

SBA is a glycosylated, tetrameric lectin with a subunit molecular weight of about 30 kDa and a high affinity for N-acetylgalactosamine.

Trypsin inhibitors affect the intestinal proteolysis reducing protein digestibility, and also increase the secretion of digestive enzymes from the pancreas leading to a loss of amino acids in the form of digestive enzymes. An example of a trypsin inhibitor is the Bowman-Birk Inhibitor, which has a molecular weight of about 8 kDa, contains 7 disulfide bridges and has two inhibitory loops specific for trypsin-like and chymotrypsin-like proteases. Other examples are the so-called Kunitz Inhibitors of Factors (e.g., the Soybean Kunitz Trypsin Inhibitor that contains one binding site for trypsin-like proteases and has a molecular weight of about 20 kDa).

The proteases for use according to the invention have been shown to hydrolyze anti-nutritional factors like SBA lectin, and the trypsin inhibitors Bowman Birk Inhibitor and The Soybean Kunitz Factor. See the experimental part, Example 5.

Thus, the invention also relates to the use of acid-stable serine proteases for hydrolyzing, or reducing the amount of, anti-nutritional factors, e.g., SBA lectin, and trypsin inhibitors, such as the Bowman Birk Inhibitor, and Kunitz Factors, such as the Soybean Kunitz Factor.

EXAMPLE 1

Screening for Acid-Stable Proteases

A large number of proteases were analyzed for stability at pH 3, with the objective of identifying proteases that have the necessary stability to pass through the acidic stomach of mono-gastric animals.

The proteases had been purified by conventional chromatographic methods such as ion-exchange chromatography, hydrophobic interaction chromatography and size exclusion chromatography (see e.g., Protein Purification, Principles, High Resolution Methods, and Applications. Editors: Jan-Christer Janson, Lars Rydén, VCH Publishers, 1989).

Protease activity was determined as follows: The protease was incubated with 1.67% Hammarsten casein at 25° C., pH 9.5 for 30 minutes, then TCA (tri-chloro acetic acid) was added to a final concentration of 2% (w/w), the mixture was filtrated to remove the sediment, and the filtrate was analyzed for free primary amino groups (determined in a colometric assay based on OPA (o-phthal-dialdehyde) by measuring the absorbance at 340 nm, using a serine standard (Biochemische Taschenbuch teil II, Springer-Verlag (1964), p. 93 and p. 102). One Casein Protease Unit (CPU) is defined as the amount of enzyme liberating 1 mmol of TCA-soluble primary amino groups per minute under standard conditions, i.e., 25° C. and pH 9.5.

The proteases were diluted to an activity of 0.6 CPU/l in water, divided in two aliquots and each aliquot was then further diluted to 0.3 CPU/l with 100 mM citrate buffer, pH 3, and 100 mM phosphate buffer, pH 7 respectively. The diluted samples were incubated at 37° C. for 1 hour, and 20 microliters of the samples were applied to holes in 1% agarose plates containing 1% skim milk. The plates (pH 7.0) were incubated at 37° C. over night and clearing zones were measured.

42 proteases performed well in this test. A number of these have been characterized, see examples 2, 6, 7 and 8. These proteases all belong to the subtilisin family of serine proteases.

EXAMPLE 2

Characterization and Comparative Study of the Subtilisin Protease Derived from Bacillus sp., NCIMB 40484

The protease derived from Bacillus sp., NCIMB 40484 was prepared as described in Example 1 of WO 93/24623.

The purpose of this characterization was to study its pH-stability, pH-activity and temperature-activity profiles, in comparison to Sub. Novo, Sub. Novo (Y217L), and SAVINASE™.

Sub. Novo is subtilisin from Bacillus amyloliquefaciens, and Sub. Novo (Y217L) is the mutant thereof that is disclosed in WO 96/05739. Sub. Novo was prepared and purified from a culture of the wild-type strain using conventional methods, whereas the mutant was prepared as described in Examples 1-2, and 15-16 of EP 130756.

SAVINASE™ is a subtilisin derived from Bacillus clausii (previously Bacillus lentus, NCIB 10309), commercially available from Novozymes A/S, Krogshoejvej, DK-2880 Bagsvaerd, Denmark. Its preparation is described in U.S. Pat. No. 3,723,250.

EXAMPLE 2A

Determination of SDS-PAGE Purity of Protease Samples

The SDS-PAGE purity of the protease samples was determined by the following procedure:

Forty microliters protease solution ($A_{280}$ concentration=0.025) was mixed with 10 microliters 50% (w/v) TCA (trichloroacetic acid) in an Eppendorf tube on ice. After half an hour on ice the tube was centrifuged (5 minutes, 0° C., 14.000×g) and the supernatant was carefully removed. Twenty microliters SDS-PAGE sample buffer (200 microliters Tris-Glycine SDS Sample Buffer (2×) (125 mM Tris/HCl, pH 6.8, 4% (w/v) SDS, 50 ppm bromophenol blue, 20% (v/v) Glycerol, LC2676 from NOVEX™)+160 microliters dist. water+20 microliters beta-mercaptoethanol+20 microliters 3 M unbuffered Tris Base (Sigma T-1503) was added to the precipitate and the tube was boiled for 3 minutes. The tube was centrifuged shortly and 10 microliter sample was applied to a 4-20% gradient Tris-Glycine precast gel from NOVEX™ (polyacrylamide gradient gel based on the Laemmli chemistry but without SDS in the gel, (Laemmli, U.K., (1970) Nature, vol. 227, pp. 680-685), EC60255). The electrophoresis was performed with Tris-Glycine running buffer (2.9 g Tris Base, 14.4 g Glycine, 1.0 g SDS, distilled water to 1 liter) in both buffer reservoirs at a 150 V constant voltage until the bromophenol blue tracking dye had reached the bottom of the gel. After electrophoresis, the gel was rinsed 3 times, 5 minutes each, with 100 ml of distilled water by gentle shaking. The gel was then gently shaked with Gelcode® Blue Stain Reagent (colloidal Comassie G-250 product from PIERCE, PIERCE cat. No. 24592) for one hour and washed by gentle shaking for 8 to 16 hours with distilled water with several changes of distilled water. Finally, the gel was dried between 2 pieces of cellophane. Dried gels were scanned with a Arcus II scanner from AGFA equipped with Fotolook 95 v2.08 software and imported to the image evaluation software CREAM™ for Windows (catalogue nos. 990001 and 990005, Kem-En-Tec, Denmark) by the File/Acquire command with the following settings (of Fotolook 95 v2.08): Original=Reflective, Mode=Color RGB, Scan resolution=240 ppi, Output resolution=120Ipi, Scale factor=100%, Range=Histogram with Global selection and Min=0 and Max=215, ToneCurve=None, Sharpness=None, Descreen=None and Flavor=None, thereby producing an *.img picture file of the SDS-PAGE gel, which was used for evaluation in CREAM™. The *.img picture file was evaluated with the menu command Analysis/1-D. Two scan lines were placed on the *.img picture file with the Lane Place Tool: A Sample scan line and a Background scan line. The Sample scan line was placed in the middle of a sample lane (with the protease in question) from just below the application slot to just above the position of the Bromphenol blue tracking dye. The Background scan line was placed parallel to the Sample scan line, but at a position in the pictured SDS-PAGE gel where no sample was applied, start and endpoints for the Background scan line were perpendicular to the start and endpoints of the Sample scan line. The Background scan line represents the true background of the gel. The width and shape of the scan lines were not adjusted. The intensity along the scan lines where now recorded with the 1-D/Scan menu command with Medium sensitivity. Using the 1-D/Editor menu command, the Background scan was subtracted from the Sample scan. Then the 1-D/Results menu command was selected and the Area % of the protease peak, as calculated by the CREAM™ software, was used as the SDS-PAGE purity of the proteases.

The following results were obtained:

| Protease | SDS-PAGE Purity (Area %) |
|---|---|
| From Bacillus sp. NCIMB 40484 | 96.3 |
| Sub. Novo | 95.5 |
| Sub. Novo (Y217L) | 96.0 |
| Savinase ® | 99.2 |

EXAMPLE 2B pH-Activity Assay

Suc-AAPF-pNA (Sigma®S-7388) was used for obtaining pH-activity profiles.

Assay buffer: 100 mM succinic acid (Merck 1.00682), 100 mM HEPES (Sigma H-3375), 100 mM CHES (Sigma C-2885), 100 mM CABS (Sigma C-5580), 1 mM $CaCl_2$, 150 mM KCl, 0.01% Triton® X-100, adjusted to pH-values 3.0, 4.0, 5.0, 6.0, 7.0, 8.0, 9.0, 10.0, or 11.0 with HCl or NaOH.

Assay temperature: 25° C.

A 300 microliter protease sample (diluted in 0.01% Triton® X-100) was mixed with 1.5 ml of the assay buffer at the respective pH value, bringing the pH of the mixture to the pH of the assay buffer. The reaction was started by adding 1.5 ml pNA substrate (50 mg dissolved in 1.0 ml DMSO and further diluted 45× with 0.01% Triton® X-100) and, after mixing, the increase in $A_{405}$ was monitored by a spectrophotometer as a measurement of the protease activity at the pH in question. The assay was repeated with the assay buffer at the other pH values, and the activity measurements were plotted as relative activity against pH. The relative activities were normalized with the highest activity (pH-optimum), i.e., setting activity at pH-optimum to 1, or to 100%. The protease samples were diluted to ensure that all activity measurements fell within the linear part of the dose-response curve for the assay.

EXAMPLE 2C pH-Stability Assay

Suc-AAPF-pNA (Sigma® S-7388) was used for obtaining pH-stability profiles.

Assay buffer: 100 mM succinic acid, 100 mM HEPES, 100 mM CHES, 100 mM CABS, 1 mM $CaCl_2$, 150 mM KCl, 0.01% Triton® X-100 adjusted to pH-values 2.0, 2.5, 3.0, 3.5, 4.0, 4.5, 5.0, 6.0, 7.0, 8.0, 9.0, 10.0 or 11.0 with HCl or NaOH.

Each protease sample (in 1 mM succinic acid, 2 mM $CaCl_2$, 100 mM NaCl, pH 6.0 and with an $A_{280}$ absorption>10) was diluted in the assay buffer at each pH value tested to $A_{280}$=1.0. The diluted protease samples were incubated for 2 hours at 37° C. After incubation, protease samples were diluted in 100 mM succinic acid, 100 mM HEPES, 100 mM CHES, 100 mM CABS, 1 mM $CaCl_2$, 150 mM KCl, 0.01% Triton® X-100, pH 9.0, bringing the pH of all samples to pH 9.0.

In the following activity measurement, the temperature was 25° C.

A 300 microliter diluted protease sample was mixed with 1.5 ml of the pH 9.0 assay buffer and the activity reaction was started by adding 1.5 ml pNA substrate (50 mg dissolved in 1.0 ml DMSO and further diluted 45× with 0.01% Triton® X-100) and, after mixing, the increase in $A_{405}$ was monitored by a spectrophotometer as a measurement of the (residual) protease activity. The 37° C. incubation was performed at the different pH-values and the activity measurements were plotted as residual activities against pH. The residual activities were normalized with the activity of a parallel incubation (control), where the protease was diluted to $A_{280}$=1.0 in the assay buffer at pH 9.0 and incubated for 2 hours at 5° C. before activity measurement as the other incubations. The protease samples were diluted prior to the activity measurement in order to ensure that all activity measurements fell within the linear part of the dose-response curve for the assay.

EXAMPLE 2D

Temperature-Activity Assay

Protazyme AK tablets were used for obtaining temperature profiles. Protazyme AK tablets are azurine dyed crosslinked casein prepared as tablets by Megazyme.

Assay buffer: 100 mM succinic acid, 100 mM HEPES, 100 mM CHES, 100 mM CABS, 1 mM $CaCl_2$, 150 mM KCl, 0.01% Tritone® X-100 adjusted to pH 9.0 with NaOH.

A Protazyme AK tablet was suspended in 2.0 ml 0.01% Triton® X-100 by gentle stirring. Five hundred microliters of this suspension and 500 microliters assay buffer were mixed in an Eppendorf tube and placed on ice. A 20 microliter protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate. By transferring the tube back to the ice bath, the assay incubation was stopped. The tube was centrifuged in an ice-cold centrifuge for a few minutes and the $A_{650}$ of the supernatant was read by a spectrophotometer. A buffer blind was included in the assay (instead of enzyme). $A_{650}$(protease)-$A_{650}$(blind) was a measurement of protease activity. The assay was performed at different temperatures and the activity measurements were plotted as relative activities against incubation temperature. The relative activities were normalized with the highest activity (temperature optimum). The protease samples were diluted to ensure that all activity measurements fell within the near linear part of the dose-response curve for the assay.

Figure 2:
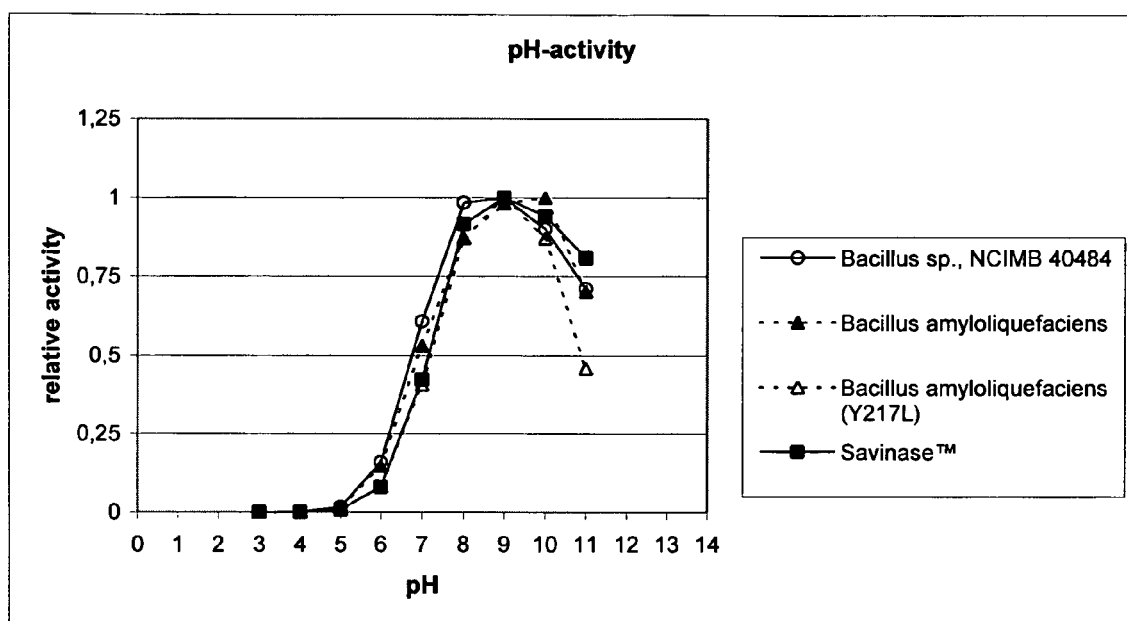
FIG. 2 shows pH-activity curves, viz. protease activity between pH 3 and pH 11, relative to the protease activity at pH-optimum, of the same four proteases.
Figure 3:
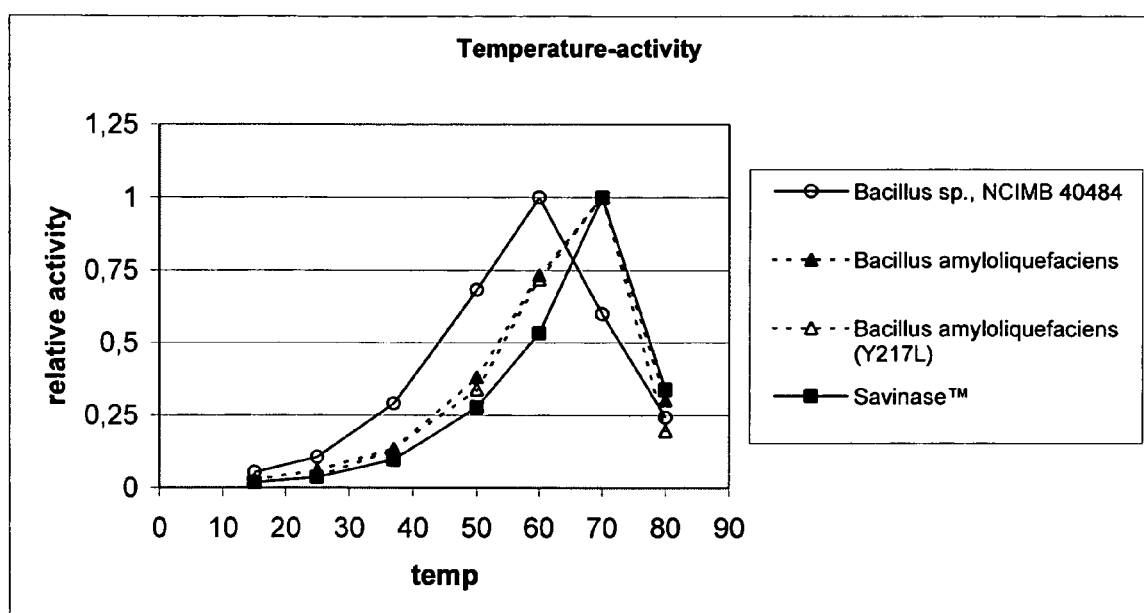
FIG. 3 shows temperature-activity curves at pH 9.0, viz. protease activity at pH 9.0 between 15° C. and 80° C., relative to protease activity at the optimum temperature, of the same four proteases.

An overview of the activity optima (pH- and temperature activity) is seen in Table 1. pH-stability, pH-activity and temperature-activity profiles are seen in FIGS. 1-3, and a detailed comparison of the pH-stability data for the proteases at acidic pH-values is seen in Table 2.

TABLE 1 pH- and temperature optima of various proteases

| Protease | pH-optimum (pNA-substrate) | Temperature-optimum at pH 9.0 (Protazyme AK) |
|---|---|---|
| From *Bacillus* sp., NCIMB 40484 | 9 | 60° C. |
| Sub. Novo[1] | 10 | 70° C. |
| Sub. Novo(Y217L)[2] | 9 | 70° C. |
| SAVINASE ™[3] | 9 | 70° C. |

TABLE 2 pH-stability of various proteases, between pH 2.0 and 5.0

| Protease | pH 2.0 | pH 2.5 | pH 3.0 | pH 3.5 | pH 4.0 | pH 4.5 | pH 5.0 |
|---|---|---|---|---|---|---|---|
| From *Bacillus* sp., NCIMB 40484 | 0.001 | 0.001 | 0.428 | 0.940 | 0.991 | 0.989 | 0.991 |
| Sub. Novo | 0.007 | 0.003 | 0.000 | 0.000 | 0.024 | 0.784 | 0.942 |
| Sub. Novo (Y217L) | 0.000 | 0.000 | 0.002 | 0.003 | 0.350 | 0.951 | 0.996 |
| Savinase ® | 0.001 | 0.001 | 0.001 | 0.003 | 0.338 | 0.929 | 0.992 |

EXAMPLE 2E

Absorption Purity of Purified Protease Samples

Determination of $A_{280}/A_{260}$ Ratio

The $A_{280}/A_{260}$ ratio of purified protease samples is determined as follows.

$A_{260}$ means the absorption of a protease sample at 260 nm in a 1 cm path length cuvette relative to a buffer blank. $A_{280}$ means the absorption of the same protease sample at 280 nm in a 1 cm path length cuvette relative to a buffer blank.

Samples of the purified proteases from Examples 2 and 6 were diluted in buffer until the $A_{280}$ reading of the spectrophotometer was within the linear part of its response curve.

The $A_{280}/A_{260}$ ratio was determined from the readings.
The following results were obtained:

| Protease/subtilisin from | $A_{280}/A_{260}$ |
|---|---|
| Sub. Novo | 2.11 |
| Sub. Novo (Y217L) | 2.12 |
| SAVINASE ™ | 2.12 |
| Bacillus sp., NCIMB 40484 | 2.19 |
| Bacillus alcalophilus, NCIMB 10438 | 1.92 |
| Fusarium oxysporum, IFO 4471 | 1.89 |
| Paecilomyces lilacinus, CBS 102449 | 1.92 |
| Acremonium chrysogenum, ATCC 48272 | 2.04 |
| Acremonium kiliense, ATCC 20338 | 1.71 |

EXAMPLE 3

Ability of the Protease Derived from Bacillus sp., NCIMB 40484 to Degrade Insoluble Parts of Soy Bean Meal (SBM)

The protease from Bacillus sp., NCIMB 40484 was tested for its ability to make the insoluble/indigestible parts of SBM accessible to digestive enzymes and/or added exogenous enzymes.

Its performance was compared to two aspartate proteases, Protease I and Protease II, prepared as described in WO 95/02044. This document also discloses their use in feed. Protease I is an Aspergillopepsin II type of protease, and Protease II an Aspergillopepsin I type of protease (both aspartate proteases, i.e., non-subtilisin proteases) from Aspergillus aculeatus (reference being made to Handbook of Proteolytic Enzymes referred to above).

The test substrate, the so-called soy remnant, was produced in a process which mimics the digestive tract of mono-gastric animals, including a pepsin treatment at pH 2, and a pancreatin treatment at pH 7.

In the pancreatin treatment step a range of commercial enzymes was added in high dosages in order to degrade the SBM components that are accessible to existing commercial enzymes.

The following enzymes, all commercially available from Novozymes A/S, Denmark, were added: ALCALASE™ 2.4L, NEUTRASE™ 0.5L, FLAVOURZYME™ 1000L, ENERGEX™ L, BIOFEED™ Plus L, PHYTASE NOVO™ L. The SBM used was a standard 48% protein SBM for feed, which had been pelletized.

After the treatment only 5% of the total protein was left in the resulting soy remnant.

FITC Labelling Protocol

The remnant was subsequently labelled with FITC (Molecular Probes, F-143) as follows: Soy remnant (25 g wet, ~5 g dry) was suspended in 100 ml 0.1 M carbonate buffer, pH 9 and stirred 1 hour at 40° C. The suspension was cooled to room temperature and treated with fluorescein 5-isothiocyanate (FITC) over night in the dark. Non-coupled probe was removed by ultrafiltration (10,000 Mw cut-off).

FITC-assay

The FITC-labelled soy remnant was used for testing the ability of the proteases to degrade the soy remnant using the following assay: 0.4 ml protease sample (with $A_{280}$=0.1) was mixed with 0.4 ml FITC-soy remnant (suspension of 10 mg/ml in 0.2 M sodium-phosphate buffer pH 6.5) at 37° C., and the relative fluorescence units (RFU 485/535 nm; excitation/monitoring wave length) measured after 0 hours, and after 22 hours incubation. Before determination of the RFU, samples were centrifuged for 1 min at 20.000× G and 250 microliter supernatant was transferred to a black micro-titer tray. Measurements were performed using a VICTOR 1420 Multilabel counter (In vitro, Denmark). RFU is generally described by Iain D. Johnson in: Introduction to Fluorescence Techniques, Handbook of Fluorescent Probes and Research Chemicals, Molecular Probes, Richard P. Haugland, $6^{th}$ edition, 1996 (ISBN 0-9652240-0-7).

A blind sample was prepared by adding 0.4 ml buffer instead of enzyme sample. $RFU_{sample} = \Delta RFU_{sample} - \Delta RFU_{blind}$, where $\Delta RFU = RFU$ (22 hours) $-RFU$ (0 hours)

The resulting FITC values ($RFU_{sample}$ values) are shown in Table 3 below. The FITC values are generally with an error margin of +/−20.000. Contrary to Protease I and Protease II, the protease derived from Bacillus sp. NCIMB 40484 degraded the soy remnant to a significant extent.

TABLE 3

Ability of proteases to degrade soy remnant

| Protease | FITC (+/−20000) |
|---|---|
| Bacillus sp., NCIMB 40484 | 61900 |
| Protease I | −9200 |
| Protease II | −1200 |

EXAMPLE 4

In vitro Testing of the Protease Derived from Bacillus sp., NCIMB 40484

The protease derived from Bacillus sp., NCIMB 40484 was tested together with other subtilisin proteases such as Sub. Novo, Sub. Novo (Y217L), SAVINASE™ and ALCALASE™ for its ability to solubilize maize-SBM (maize-Soy Bean Meal) proteins in an automated in vitro digestion system (simulating digestion in monogastric animals). For the blank treatments, maize-SBM was incubated in the absence of exogenous subtilisin-like proteases.

The in vitro system consisted of 30 flasks in which maize-SBM substrate was initially incubated with HCl/pepsin—simulating gastric digestion—and subsequently with pancreatin—simulating intestinal digestion. At the end of the gastric incubation period samples of in vitro digesta were removed and analyzed for solubilized protein.

Substrates 10 g maize-SBM diet with a maize-SBM ratio of 6:4 (w/w) was used. The protein content was 43% (w/w) in SBM and 8.2% (w/w) in maize meal. The total amount of protein in 10 g maize-SBM diet was 2.21 g.

Digestive Enzymes

Pepsin (Sigma P-7000; 539 U/mg, solid), pancreatin (Sigma P-7545; 8×U.S.P. (US Pharmacopeia)).

Outline of in vitro Digestion Procedure

| Components added to flask | pH | Temp. | Time course | Simulated digestion phase |
|---|---|---|---|---|
| 10 g maize-SBM diet (6:4), HCl/pepsin (3000 U/g diet), protease (0.1 mg protease enzyme protein/g diet) | 3.0 | 40° C. | t = 0 min | Gastric |

-continued

| Components added to flask | pH | Temp. | Time course | Simulated digestion phase |
|---|---|---|---|---|
| NaOH | 6.8 | 40° C. | t = 60 min | Intestinal |
| NaHCO$_3$/pancreatin (8 mg/g diet) | 6.8 | 40° C. | t = 90 min | |
| Stop incubation, remove aliquot | 7.0 | 0° C. | t = 330 min | |

Enzyme Protein Determinations

The amount of protease enzyme protein is calculated on the basis of the A$_{280}$ values and the amino acid sequences (amino acid compositions) using the principles outlined in S. C. Gill & P. H. von Hippel, Analytical Biochemistry 182, 319-326 (1989).

Experimental Procedure for in vitro Model 1. 10 g of substrate is weighed into a 100 ml flask.
2. At time 0 min, 46 ml HCl (0.1 M) containing pepsin (3000 U/g diet) and 1 ml of protease (0.1 mg enzyme protein/g diet) are added to the flask while mixing. The flask is incubated at 40° C.
3. At time 30 min, pH is measured.
4. At time 45 min, 16 ml of H$_2$O is added.
5. At time 60 min, 7 ml of NaOH (0.39 M) is added.
6. At time 90 min, 5 ml of NaHCO$_3$ (1 M) containing pancreatin (8.0 mg/g diet) is added.
7. At time 120 min, pH is measured.
8. At time 300 min, pH is measured.
9. At time 330 min, samples of 30 ml are removed and placed on ice before centrifugation (10000×g, 10 min, 4° C.). Supernatants are removed and stored at −20° C.

Estimation of Solubilized Protein by Gelfiltration HPLC

The content of solubilized protein in supernatants from in-vitro digested samples was estimated by quantifying crude protein (CP) using gelfiltration HPLC. Supernatants were thawed, filtered through 0.45 micro-m polycarbonate filters (Sartorius) and diluted (1:50, v/v) with H$_2$O. Diluted samples were chromatographed by HPLC using a Superdex Peptide PE (7.5×300 mm) gelfiltration column (Global). The eluent used for isocratic elution was 50 mM sodium phosphate buffer (pH 7.0) containing 150 mM NaCl. The total volume of eluent per run was 26 ml and the flow rate was 0.4 ml/min. Elution profiles were recorded at 214 nm and the total area under the profiles was determined by integration. To estimate protein content from integrated areas, a calibration curve ($R^2$=0.9993) was made from a dilution series of an in vitro digested reference maize-SBM sample with known total protein content. The protein determination in this reference sample was carried out by the Kjeldahl method (determination of % nitrogen; A.O.A.C. (1984) Official Methods of Analysis 14$^{th}$ ed., Washington D.C.).

Results

The results, i.e., the effect of the various proteases on protein solubility in vitro, are shown in Table 4 below.

The calculation of relative amounts of solubilized protein is based on the total amount of protein in 10 g maize-SBM diet (2.21 g protein) dissolved in a total volume of 75 ml during the in vitro digestion reaction. Assuming complete protein solubilization (100%), the protein content in supernatants would be 2.95% weight per volume.

The results were analyzed by one-way analysis of variance: P=0.0001). SD=Standard Deviation; n=the number of replicas per treatment (n=5).

The protease derived from *Bacillus* sp. NCIMB 40484 has a significantly better effect on protein solubilization as compared to the other proteases.

TABLE 4

| Enzyme | Soluble CP (% of total) | SD |
|---|---|---|
| Protease from *Bacillus* sp. NCIMB 40484 | 78.8[A] | 0.48 |
| Sub. Novo | 76.7[B] | 0.37 |
| ALCALASE ™ | 73.9[C] | 1.04 |
| Sub. Novo (Y217L) | 75.8[B] | 0.91 |
| SAVINASE ™ | 75.8[B] | 0.85 |
| Blank | 76.6[B] | 0.88 |

[A,B,C]Values not sharing a common index letter differ significantly (P < 0.05)

EXAMPLE 5

Degradation of the Lectin SBA and the Soybean Bowman-Birk and Kunitz Inhibitors

The ability of the protease from *Bacillus* sp., NCIMB 40484 to hydrolyze soybean agglutinin (SBA) and the soy Bowman-Birk and Kunitz trypsin inhibitors was tested.

Pure SBA (Fluka 61763), Bowman-Birk Inhibitor (Sigma T-9777) or Kunitz Inhibitor (Trypsin Inhibitor from soybean, Boehringer Mannheim 109886) was incubated with the protease for 2 hours, 37° C., at pH 6.5 (protease: anti-nutritional factor=1:10, based on A$_{280}$). Incubation buffer: 50 mM dimethyl glutaric acid, 150 mM NaCl, 1 mM CaCl$_2$, 0.01% Triton X-100, pH 6.5.

The ability of the protease to degrade SBA and the protease inhibitors was estimated from the disappearance of the native SBA or trypsin inhibitor bands and appearance of low molecular weight degradation products on SDS-PAGE gels. Gels were stained with Coomassie blue and band intensity determined by scanning.

The results, as % of anti-nutritional factor degraded, are shown in Table 5 below.

It is contemplated that the ability to degrade the anti-nutritional factors in soy can also be estimated by applying the Western technique with antibodies against SBA, Bowman-Birk Inhibitor or Kunitz Inhibitor after incubation of soybean meal with the candidate proteases (see WO 98/56260).

TABLE 5

| Protease derived from | SBA | Bowman-Birk Inhibitor | Kunitz Inhibitor |
|---|---|---|---|
| *Bacillus* sp., NCIMB 40484 | 21 | 41 | 100 |

EXAMPLE 6

Preparation of Further Acid-Stable Subtilisins

Preparation of the *Bacillus alcalophilus* Protease

*Bacillus alcalophilus*, NCIMB 10438 was inoculated from a freeze dried culture into shake flasks each containing 100 ml BPX medium with the following composition: potato starch 100 g/l, barley flour 50 g/l, BAN 800 MG (obtainable from Novozymes A/S) 0.05 g/l, sodium caseinate 10 g/l, soy meal 20 g/l, di-sodiumphosphate 9 g/l, Pluronic PE 6100 0.1 ml/l in tap water. The pH was adjusted to 9.7 with 10 ml 1 M sodium sesquicarbonate in each shake flask before inoculation. The strain was fermented for 4 days at 30° C. at 300 rpm. From this culture new shake flasks containing 100 ml BPX medium were inoculated and fermented for 3 days.

Purification

The culture broth was centrifuged at 10000×g for 30 minutes in 1 liter beakers. The supernatants were combined and further clarified by a filtration though a Seitz K-250 depth filter plate. The clear filtrate was concentrated by ultrafiltration on a 3 kDa cut-off polyether sulfone cassette (Filtron). The concentrated enzyme was transferred to 50 mM $H_3BO_3$, 5 mM 3,3'-dimethyl glutaric acid, 1 mM $CaCl_2$, pH 7 (Buffer A) on a G25 Sephadex column (Amersham Pharmacia Biotech), and applied to a Bacitracin agarose column (Upfront Chromatography A/S) equilibrated in Buffer A. After washing the Bacitracin column with Buffer A to remove unbound protein, the protease was eluted from the column using Buffer A supplemented with 25% 2-propanol and 1 M sodium chloride. The fractions from the Bacitracin column with protease activity were pooled and transferred to 20 mM $CH_3COOH$/NaOH, 1 mM $CaCl_2$, pH 5 (Buffer B) by G25 Sephadex chromatography. The buffer exchanged protease pool was applied to a SOURCE 30S column (Amersham Pharmacia Biotech) equilibrated in Buffer B. After washing the SOURCE 30S column with Buffer B, the protease was eluted with an increasing linear NaCl gradient (0 to 0.5 M) in Buffer B. Fractions from the column were tested for protease activity and protease containing fractions were analyzed by SDS-PAGE. Pure fractions were pooled and used for further characterization.

Preparation of Other Acid-Stable Subtilisins

The proteases of *Fusarium oxysporum*, IFO 4471, *Bacillus alcalophilus*, NCIMB 10438, *Paecilomyces lilacinus*, CBS 102449, *Acremonium chrysogenum*, ATCC 48272, and *Acremonium kiliense*, ATCC 20388 were prepared using conventional methods, as generally described above for the protease of *Bacillus alcalophilus*, NCIMB 10438.

Sequences

The following partial amino acid sequences were determined:

SEQ ID NO: 1

N-terminal of the protease derived from *Acremonium chrysogenum*, ATCC 48272:

ALVTQNGAPWGLGTISHRQPGSTSYIY;

SEQ ID NO: 2

N-terminal of the protease derived from *Bacillus alcalophilus*, NCIMB 10438:

NQVTPWGITRVQAPTAW;

SEQ ID NO: 3

N-terminal of the protease derived from *Paecilomyces lilacinus*, CBS 102449:

AYTQQPGAPWGLGRISH;

SEQ ID NO: 4

N-terminal of the protease derived from *Fusarium oxysporum*, IFO 4471:

ALTTQSGATWGLGTVSHRSRGS.

The amino acid sequence of the protease derived from *Bacillus* sp., NCIMB 40484 (SEQ ID NO: 5), had been previously determined (see U.S. Pat. No. 5,650,326, SEQ ID NOs: 4, 6 and 8).

A search in public protein databases for related sequences revealed the following:

SEQ ID NO: 6

Geneseqp/r65936 (referring to the protease of *Paecilomyces lilacinus*, CBS 143.75 of EP 623672)—related to SEQ ID NO: 3;

SEQ ID NO: 7

Geneseqp/r74334 (referring to the protease of *Bacillus* sp., THS-1001 of JP-07095882)—related to SEQ ID NO: 2.

The strains of *Paecilomyces lilacinus* and *Aspergillus* sp. have been deposited according to the Budapest Treaty on the International, Recognition of the Deposit of Microorganisms for the Purposes of Patent Procedure at the Centraalbureau voor Schimmelcultures, P.O. Box 273, 3740 AG Baarn, The Netherlands, (CBS), and at DSMZ-Deutsche Sammlung von Mikroorganismen und Zellkulturen GmbH, Mascheroder Weg 1b, D-38124 Braunschweig, Germany, respectively, as follows:

Deposit date: 17.01.00
CBS No.: *Aspergillus* sp., CBS 102448
Deposit date: 17.01.00
CBS No.: *Paecilomyces lilacinus*, CBS 102449

EXAMPLE 7

Characterization and Comparative Study of Further Subtilisin Proteases

The proteases prepared from *Bacillus alcalophilus*, NCIMB 10438, *Fusarium oxysporum*, IFO 4471, *Paecilomyces lilacinus*, CBS 102449, *Acremonium chrysogenum*, ATCC 48272, *Acremonium kiliense*, ATCC 20338 are all subtilisins.

The purity of the protease samples was determined as described in Example 2.

The following results were obtained:

| Protease | SDS-PAGE Purity (Area %) |
|---|---|
| *Bacillus alcalophilus*, NCIMB 10438 | 100.0 |
| *Fusarium oxysporum*, IFO 4471 | n.d. |
| *Paecilomyces lilacinus*, CBS 102449 | 98.3 |
| *Acremonium chrysogenum*, ATCC 48272 | 98.6 |
| *Acremonium kiliense*, ATCC 20338 | n.d. | n.d. = not determined

Assays

The pH-activity, pH-stability and temperature-activity assays are described in Example 2 (the pNA substrate Suc-AAPF-pNA (Sigma S-7388) was used for all of the proteases for pH-activity and -stability profiles, whereas Protazyme AK tablets were used for the temperature profiles).

Figure 4:
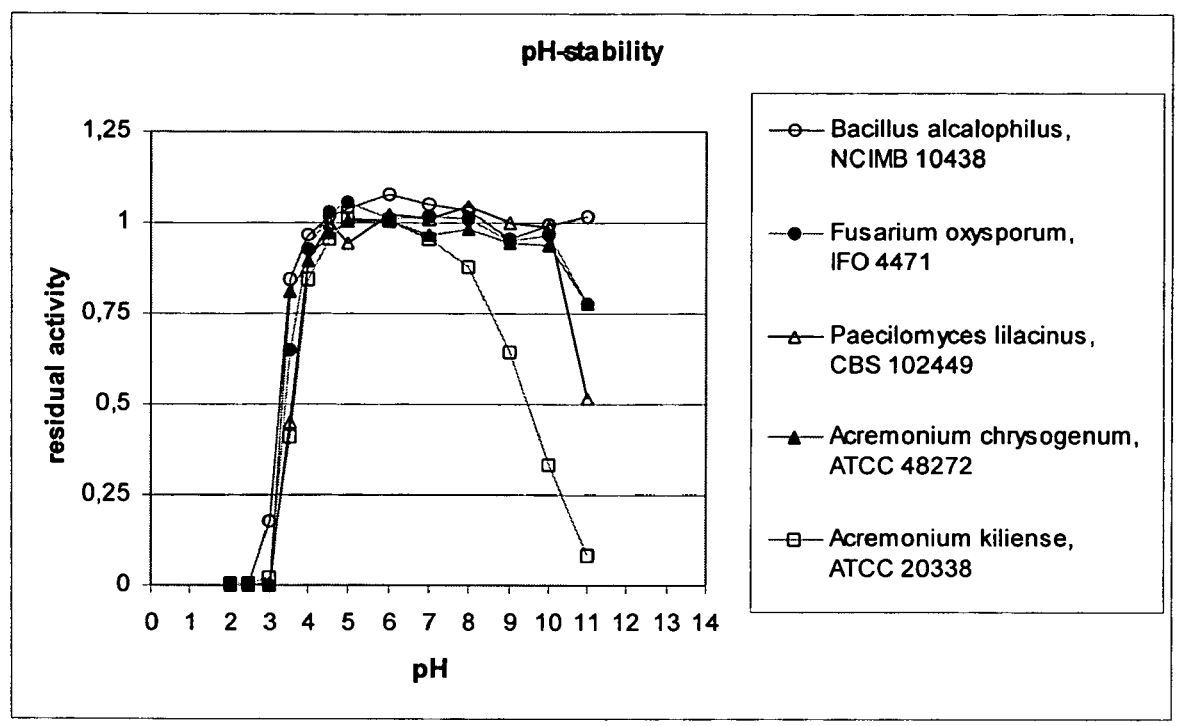
FIG. 4 shows pH-stability curves similar to FIG. 1 but for five other acid-stable proteases of the subtilisin family derived from *Bacillus alcalophilus*, NCIMB 10438, *Fusarium oxysporum*, IFO 4471, *Paecilomyces lilacinus*, CBS 102449, *Acremonium chrysogenum*, ATCC 48272, *Acremonium kiliense*, ATCC 20338.
Figure 5:
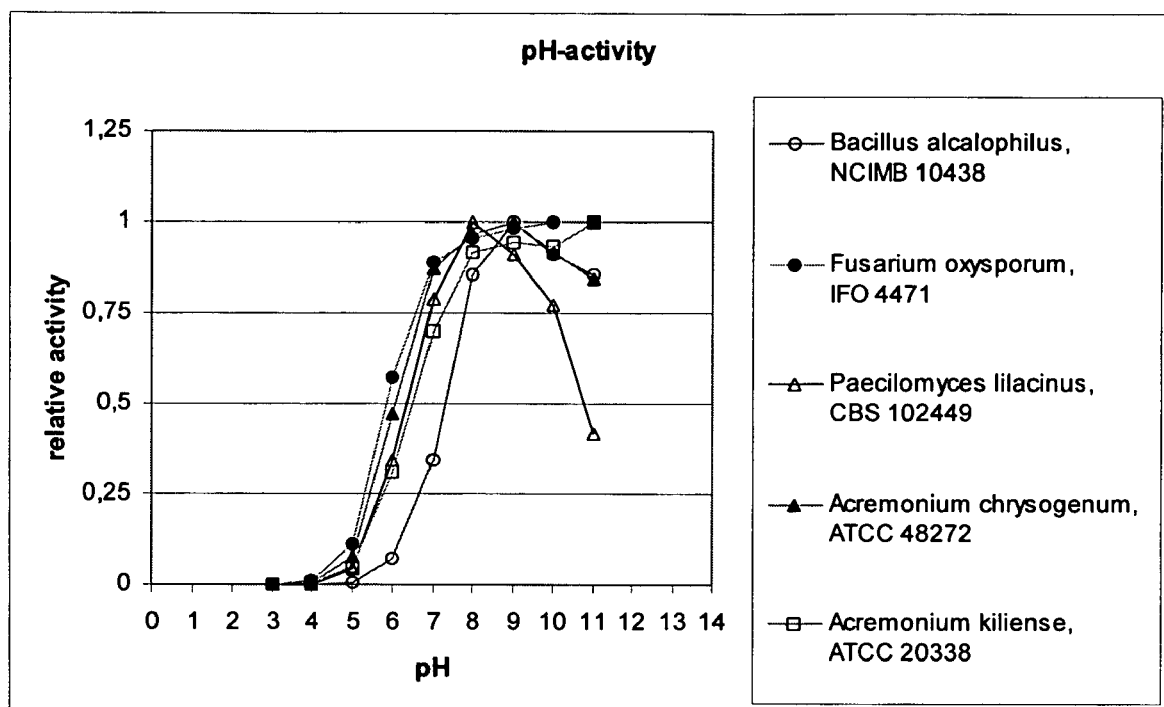
FIG. 5 shows pH-activity curves similar to FIG. 2 but for the same proteases as in FIG. 4.
Figure 6:
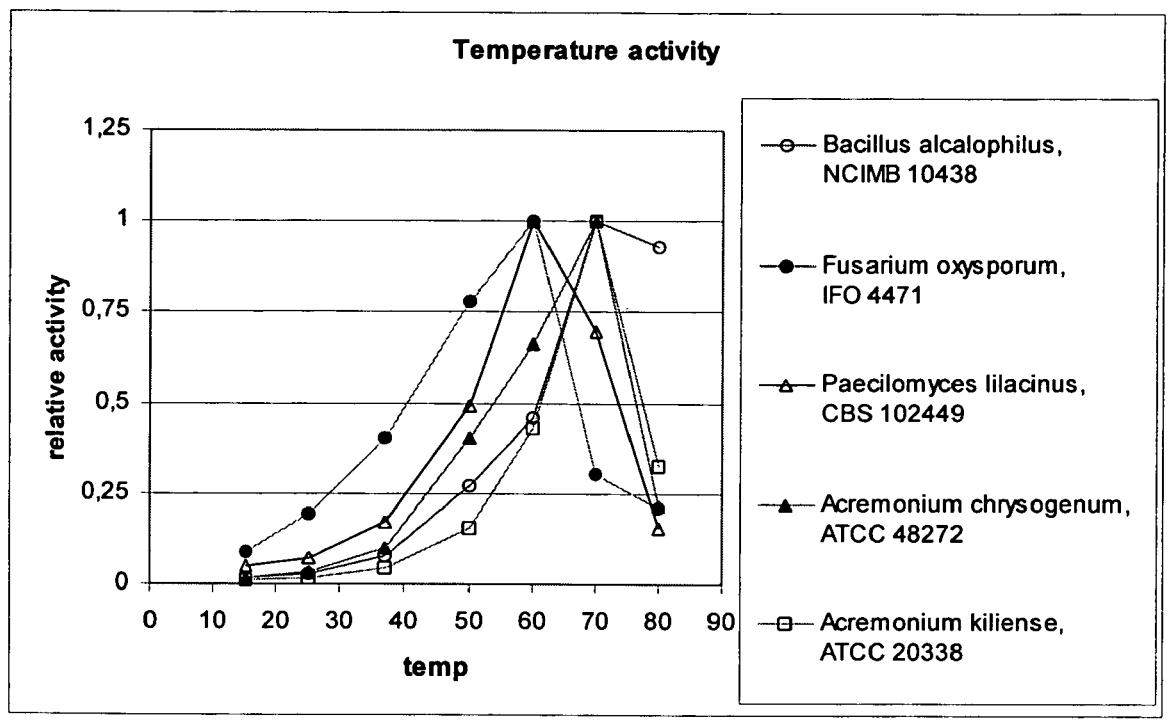
FIG. 6 shows temperature activity curves at pH 9.0 similar to FIG. 3 but for the same proteases as in FIG. 4.

An overview of the activity optima (pH- and temperature activity) is seen in Table 6. pH-stability, pH-activity and temperature-activity profiles are seen in FIGS. 4-6, and a detailed comparison of the pH-stability data for the proteases at acidic pH-values is seen in Table 7.

TABLE 6 pH- and temperature optima of various proteases

| Protease | pH-optimum | Temperature-optimum (° C.) |
|---|---|---|
| *Bacillus alcalophilus*, NCIMB 10438 | 9 | 70 |
| *Fusarium oxysporum*, IFO 4471 | 11 | 60 |
| *Paecilomyces lilacinus*, CBS 102449 | 8 | 60 |

TABLE 6-continued pH- and temperature optima of various proteases

| Protease | pH-optimum | Temperature-optimum (° C.) |
|---|---|---|
| *Acremonium chrysogenum*, ATCC 48272 | 9 | 70 |
| *Acremonium kiliense*, ATCC 20338 | 11 | 70 |

TABLE 7 pH-stability of various proteases, between pH 2.0 and 5.0

| | pH | | | | | | |
|---|---|---|---|---|---|---|---|
| Protease | 2.0 | 2.5 | 3.0 | 3.5 | 4.0 | 4.5 | 5.0 |
| *Bacillus alcalophilus*, NCIMB 10438 | 0.007 | 0.005 | 0.175 | 0.844 | 0.965 | 1.017 | 1.038 |
| *Fusarium oxysporum*, IFO 4471 | 0.000 | 0.000 | 0.003 | 0.649 | 0.929 | 1.030 | 1.056 |
| *Paecilomyces lilacinus*, CBS 102449 | 0.002 | 0.003 | 0.005 | 0.450 | 0.897 | 1.000 | 0.947 |
| *Acremonium chrysogenum*, ATCC 48272 | 0.002 | 0.001 | 0.001 | 0.809 | 0.894 | 0.972 | 1.005 |
| *Acremonium kiliense*, ATCC 20338 | 0.008 | 0.003 | 0.023 | 0.412 | 0.843 | 0.955 | 1.009 |

EXAMPLE 8

Inhibition of Proteases with *Streptomyces* Subtilisin Inhibitor (SSI)

pNA substrate: Suc-AAPF-pNA (Sigma® S-7388) was used for measuring residual activity after inhibition.

Assay buffer: 100 mM succinic acid (Merck 1.00682), 100 mM HEPES (Sigma H-3375), 100 mM CHES (Sigma C-2885), 100 mM CABS (Sigma C-5580), 1 mM $CaCl_2$, 150 mM KCl, 0.01% Triton® X-100, pH 9.0.

Assay temperature: 25° C.

SSI was purified from a *Streptomyces albogriseolus* FERM P-1205 (S-3253) fermentation supernatant by chromatography. The used SSI preparation had a purity above 95%—the purity was determined by the procedure described in Example 2A. Alternatively, SSI can be obtained from Wako in Japan, catalog no. 303-05201, manufactured by Daiwa Kasei K. K.

Before the below inhibition assay, SSI was diluted in 0.01% Triton X-100 to $A_{280}$ concentration=0.010.

Protease: The used protease had a purity above 95%—the purity was determined by the procedure described in Example 2A. Before the below inhibition assay, the protease was diluted in 0.01% Triton X-100 to $A_{280}$ concentration=0.010.

The inhibition of the proteases by the *Streptomyces* Subtilisin Inhibitor (SSI) was determined by the following procedure:

A 300 microliter protease sample ($A_{280}$ concentration=0.010) was mixed with 300 µl SSI ($A_{280}$ concentration=0.010) and 1.5 ml Assay buffer. After 15 minutes incubation at room temperature, the residual activity was measured by adding 1.5 ml pNA substrate (50 mg dissolved in 1.0 ml DMSO and further diluted 45× with 0.01% Triton® X-100) and, after mixing, the increase in $A_{405}$ was monitored by a spectrophotometer. As a control (no SSI), 300 µl 0.01% Triton X-100 was used instead of SSI.

The residual activity was normalized with the control activity (no SSI), i.e., no inhibition by SSI will give 100% residual activity and full inhibition by SSI will give 0% residual activity.

The following results were obtained:

| Protease, subtilisin from | Residual activity (%) |
|---|---|
| *Bacillus* sp., NCIMB 40484 | 4.3 |
| *Bacillus amyloliquefaciens* | 0.1 |
| *Bacillus amyloliquefaciens* (Y217L) | 0.0 |
| *Bacillus clausii* (Savinase ®) | 0.0 |
| *Bacillus alcalophilus*, NCIMB 10438 | 0.0 |
| *Fusarium oxysporum* IFO 4471 | 0.1 |
| *Paecilomyces lilacinus*, CBS 102449 | 0.1 |
| *Acremonium chrysogenum*, ATCC 48272 | 0.1 |
| *Acremonium kiliense*, ATCC 20338 | n.d.* |

*not determined

EXAMPLE 9

Ability of Further Acid-Stable Subtilisins to Degrade Insoluble Parts of Soy Bean Meal (SBM)

The further acid-stable subtilisins prepared as described in Example 6 were tested as described in Example 3 for their ability to make the insoluble/indigestible parts of SBM accessible to digestive enzymes and/or added exogenous enzymes.

The results obtained are shown in Table 8 below. For comparison, the results obtained in Example 3 for proteases I and II are included also in Table 8.

TABLE 8

Ability of further proteases to degrade soy remnant

| Protease, subtilisin from | FITC/(+/−20000) |
|---|---|
| *Bacillus alcalophilus*, NCIMB 10438 | 81300 |
| *Fusarium oxysporum*, IFO 4471 | 102200 |
| *Paecilomyces lilacinus*, CBS 102449 | 98700 |
| *Acremonium chrysogenum*, ATCC 48272 | 89600 |
| *Acremonium kiliense*, ATCC 20338 | 94600 |
| Protease I | −9200 |
| Protease II | −1200 |

EXAMPLE 10

Effects of the Acid-Stable Subtilisin Derived from *Bacillus* sp. NCIMB 40484 on the Growth Performance of Broiler Chickens The trial was carried out at the Roche Research Center for Animal Nutrition (CRNA, F-68305 Village-Neuf, France) in accordance with the official French instructions for experiments with live animals. Day-old broiler chickens ('Ross PM3'), separated by sex, were supplied by a commercial hatchery.

The chickens were housed in wire-floored battery cages, which were kept in an environmentally controlled room. Feed and tap water was provided ad libitum.

On day 8, the chickens were divided by weight into groups of 6 birds, which were allocated to either the control treatment, receiving the experimental diet without enzymes, or to the enzyme treatment, receiving the experimental diet supplemented with 100 mg enzyme protein of the *Bacillus* sp., NCIMB 40484 protease per kg feed.

Each treatment was replicated with 12 groups, 6 groups of each sex. The groups were weighed on days 8 and 29. The feed consumption of the intermediate period was determined and body weight gain and feed conversion ratio were calculated.

The experimental diet based on maize starch and soybean meal (44% crude protein) as main ingredients (Table 9) was produced in the CRNA. The feed was pelleted (die configuration: 3×20 mm) at about 70° C. An appropriate amount of the *Bacillus* sp., NCIMB 40484 protease was diluted in a fixed quantity of water and sprayed onto the pelleted feed. For the control treatment, adequate amounts of water were used to handle the treatments in the same way.

For the statistical evaluation, a two factorial analysis of variance (factors: treatment and sex) was carried out, using the GLM procedure of the SAS package (SAS Institute Inc., 1985). Where significant treatments effects (p<0.05) were indicated, the differences between treatment means were analyzed with the Duncan test. Due to technical reasons, one cage of the enzyme treatment was excluded from the statistical evaluation.

In Table 2 the results of the growth performance of the broiler chickens from day 8 to day 29 are listed. There were no interactions between treatment and sex, therefore the pooled results of both sexes are presented. The supplementation of the experimental diet with *Bacillus* sp., NCIMB 40484 protease improved weight gain numerically by 6.6%. The addition of the protease increased the feed intake slightly by 3.1%. *Bacillus* sp., NCIMB 40484 protease improved the feed conversion of the broiler chickens significantly by 3.4%.

Taking into consideration that maize starch is a highly digestible ingredient, it can be assumed that the observed effects were mainly due to the action of the enzymes on the soybean meal. Therefore, the results indicated that the nutritive value of the soybean meal was improved by the *Bacillus* sp., NCIMB 40484 protease.

In conclusion, the study demonstrated that supplementation of broiler feed containing high amounts of soybean meal with the *Bacillus* sp., NCIMB 40484 protease at 100 mg enzyme protein/kg feed resulted in a numerical increase of weight gain and a significant improvement of feed conversion.

REFERENCES

EEC (1986): Directive de la Commission du 9 avril 1986 fixant la méthode de calcul de la valeur énergetique des aliments composés destinés à la volaille. Journal Officiel des Communautés Européennes, L130, 53-54

SAS Institute Inc. (1985): SAS® User's Guide, Version 5 Edition. Cary N.C.

TABLE 9

Composition of the experimental diet

| Ingredients (%): | |
|---|---|
| Maize starch | 45.80 |
| Soybean meal 44[1] | 44.40 |
| Tallow | 3.20 |
| Soybean oil | 1.00 |
| DL-Methionine | 0.18 |
| MCP | 0.76 |
| Salt | 0.05 |
| Binder | 1.00 |

TABLE 9-continued

Composition of the experimental diet

| | |
|---|---|
| Vitamin and mineral premix | 3.55 |
| Avatec ® 15% CC[2] | 0.06 |
| Analyzed content: | |
| Crude protein (%) | 19.3 |
| ME, N-corrected (MJ/kg)[3] | 12.2 |
| Crude fat (%) | 5.3 |

[1]analyzed content: 90.6% dry matter, 45.3% crude protein, 2.0% crude fat, 4.9% crude fibre
[2]corresponded to 90 mg lasalocid-Na/kg feed as anticoccidial
[3]calculated on the basis of analyzed nutrients content (EC-equation; EEC, 1986)

Supplier of Feed Ingredients
Maize starch: Roquettes Frères, F-62136 Lestrem, France
Soybean meal 44: Rekasan GmbH, D-07338 Kaulsdorf, Germany
Tallow: Fondoirs Gachot SA, F-67100 Strasbourg, France
Soybean oil: Ewoco Sari, F-68970 Guemar, France
DL-Methionine: Produit Roche SA, F-92521 Neuilly-sur-Seine, France
MCP: Brenntag Lorraine, F-54200 Toul, France
Salt: Minoterie Moderne, F-68560 Hirsingue, France
Binder: Minoterie Moderne, F-68560 Hirsingue, France
Premix (AM vol chair NS 4231): Agrobase, F-01007 Bourg-en-Bresse, France
Avatec: Produit Roche SA, F-92521 Neuilly-sur-Seine, France

TABLE 10

Performance of broiler chickens from days 8 to 29
Pooled results of both sexes; mean ± st. dev.

| | Product | |
|---|---|---|
| | Control | *Bacillus* sp., NCIMB 40484 protease |
| Dose per kg feed | 0 | 100 mg enzyme protein |
| Cages × birds | 12 × 6 | 11 × 6[1] |
| Weight gain | 1155$^A$ | 1231$^A$ |
| (g/bird) | ±94 | ±98 |
| (%) | 100.0 | 106.6 |
| Feed intake | 1941$^A$ | 2002$^A$ |
| (g/bird) | ±108 | ±145 |
| (%) | 100.0 | 103.1 |
| Feed conversion | 1.684$^A$ | 1.627$^B$ |
| (g feed/g gain) | ±0.069 | ±0.031 |
| (%) | 100.0 | 96.6 |

Means within a row, not sharing a common superscript are significantly different (p < 0.05)
[1]Due to technical reasons, one cage was excluded from the statistical evaluation

EXAMPLE 11

Premix and Diets for Turkey and Salmonids Supplemented with Acid-Stable Subtilisin Protease A premix of the following composition is prepared (content per kilo):

| | | |
|---|---|---|
| 5000000 | IE | Vitamin A |
| 1000000 | IE | Vitamin D3 |
| 13333 | mg | Vitamin E |

-continued

| | | |
|---|---|---|
| 1000 | mg | Vitamin K3 |
| 750 | mg | Vitamin B1 |
| 2500 | mg | Vitamin B2 |
| 1500 | mg | Vitamin B6 |
| 7666 | mg | Vitamin B12 |
| 12333 | mg | Niacin |
| 33333 | mg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |

To this premix is added *Bacillus* sp., NCIMB 40484 protease prepared as described in Example 2 in an amount corresponding to 10 g protease enzyme protein/kg.

Pelleted turkey starter and grower diets with a composition as shown in the below table (on the basis of Leeson and Summers, 1997 but recalculated without meat meal by using the AGROSOFT®, optimisation program) and with 100 mg protease enzyme protein per kg are prepared as follows:

Milled maize, Soybean meal, Fish-meal and Vegetable fat are mixed in a cascade mixer. Limestone, calcium phosphate and salt are added, together with the above premix in an amount of 10 g/kg diet, followed by mixing. The resulting mixture is pelleted (steam conditioning followed by the pelleting step).

| | Starter diet, g/kg | Grower, g/kg | Finisher |
|---|---|---|---|
| Ingredient | | | |
| Maize | 454.4 | 612.5 | 781.0 |
| Soybean meal | 391 | 279 | 61.7 |
| Fish meal | 70 | 29.9 | 70 |
| Vegetable fat | 21 | 21 | 46 |
| Limestone | 19 | 16.9 | 9 |
| Calcium phosphate | 30 | 25.9 | 16.8 |
| Salt (NaCl) | 2 | 2 | 2 |
| Vitamin and mineral premix | 10 | 10 | 10 |
| Lysine | 1.3 | 1.49 | |
| Methionine | 1.3 | 1.3 | 3.6 |
| Calculated nutrients | | | |
| Crude protein g/kg | 279 | 213 | 152 |
| Metabolizable energy MJ/kg | 12.3 | 12.7 | 14.1 |
| Calcium, g/kg | 15.8 | 12.7 | 9 |
| Available Phosphorus, g/kg | 8.2 | 6.4 | 4.6 |
| Lysine, g/kg | 17.6 | 12.8 | 7.5 |
| Methionine, g/kg | 6.1 | 4.9 | 6.9 |

Two diets for Salmonids are also prepared, as generally outlined above. The actual compositions are indicated in the Table below (compiled from Refstie et al (1998), Aquaculture, vol. 162, p.301-302). The estimated nutrient content is recalculated by using the Agrosoft® feed optimisation program.

The protease derived from *Bacillus* sp. NCIMB 40484, prepared as described in Example 2, is added to the diets in an amount corresponding to 100 mg protease enzyme protein per kg.

| | Conventional diet with fish meal | Alternative diet with soybean meal |
|---|---|---|
| Ingredient | | |
| Wheat | 245.3 | 75.2 |
| Fish meal | 505.0 | 310.0 |
| Soybean meal | — | 339.0 |
| Fish oil | 185.0 | 200.0 |
| DL-Methionine | 13.9 | 23.0 |
| Mono-Calcium phosphate | — | 2.0 |
| Vitamin and Mineral premix + pellet binder and astaxanthin | 50.8 | 50.8 |
| Calculated nutrients (fresh weight basis) | | |
| Crude protein g/kg | 401 | 415 |
| Crude fat g/kg | 232 | 247 |
| Metabolisable energy MJ/kg | 16.9 | 16.5 |
| Calcium, g/kg | 13.9 | 9.8 |
| Phosphorus, g/kg | 10.8 | 9.0 |
| Lysine, g/kg | 27.7 | 26.7 |
| Methionine, g/kg | 24.4 | 31.6 |

EXAMPLE 12

Determination of Purity of Protease-Containing Enzyme Products

The purity of protease-containing enzyme products, e.g., protease preparations such as commercial multi-component enzyme products, can be determined by a method based on the fractionation of the protease-containing enzyme product on a size-exclusion column. Size-exclusion chromatography, also known as gel filtration chromatography, is based on a porous gel matrix (packed in a column) with a distribution of pore sizes comparable in size to the protein molecules to be separated. Relatively small protein molecules can diffuse into the gel from the surrounding solution, whereas larger molecules will be prevented by their size from diffusing into the gel to the same degree. As a result, protein molecules are separated according to their size with larger molecules eluting from the column before smaller ones.

Protein Concentration Assay

The protein concentration in protease-containing enzyme products is determined with a BCA protein assay kit from PIERCE (identical to PIERCE cat. No.23225). The sodium salt of Bicinchoninic acid (BCA) is a stable, water-soluble compound capable of forming an intense purple complex with cuprous ions ($Cu^{1+}$) in an alkaline environment. The BCA reagent forms the basis of the BCA protein assay kit capable of monitoring cuprous ions produced in the reaction of protein with alkaline $Cu^{2+}$ (Biuret reaction). The color produced from this reaction is stable and increases in a proportional fashion with increasing protein concentrations (Smith, P. K., et al. (1985), Analytical Biochemistry, vol. 150, pp. 76-85). The BCA working solution is made by mixing 50 parts of reagent A with 1 part reagent B (Reagent A is PIERCE cat. No. 23223, contains BCA and tartrate in an alkaline carbonate buffer; reagent B is PIERCE cat. No. 23224, contains 4% $CuSO_4 \cdot 5H_2O$). Three hundred microliter sample is mixed with 3.0 ml BCA working solution. After 30 minutes at 37° C., the sample is cooled to room temperature and $A_{490}$ is read as a measure of the protein concentration in the sample. Dilutions of Bovine serum albumin (PIERCE cat. No. 23209) are included in the assay as a standard.

Sample Pre-Treatment

If the protease-containing enzyme product is a solid, the product is first dissolved/suspended in 20 volumes of 100 mM $H_3BO_3$, 10 mM 3,3'-dimethylglutaric acid, 2 mM $CaCl_2$, pH 6 (Buffer A) for at least 15 minutes at 5° C., and if the enzyme at this stage is a suspension, the suspension is filtered through a 0.45 micron filter to give a clear solution. The solution is from this point treated as a liquid protease-containing enzyme product.

If the protease-containing enzyme product is a liquid, the product is first dialyzed in a 6-8000 Da cut-off SpectraPor dialysis tube (cat. no. 132 670 from Spectrum Medical Industries) against 100 volumes of Buffer A+150 mM NaCl (Buffer B) for at least 5 hours at 5° C., to remove formulation chemicals that could give liquid protease-containing enzyme products a high viscosity, which is detrimental to the size-exclusion chromatography.

The dialyzed protease-containing enzyme product is filtered through a 0.45 micron filter if a precipitate was formed during the dialysis. The protein concentration in the dialyzed enzyme product is determined with the above described protein concentration assay and the enzyme product is diluted with Buffer B, to give a sample ready for size-exclusion chromatography with a protein concentration of 5 mg/ml. If the enzyme product has a lower than 5 mg/ml protein concentration after dialysis, it is used as is.

Size-Exclusion Chromatography

A 300 ml HiLoad26/60 Superdex75pg column (Amersham Pharmacia Biotech) is equilibrated in Buffer B (Flow: 1 ml/min). 1.0 ml of the protease-containing enzyme sample is applied to the column and the column is eluted with Buffer B (Flow: 1 ml/min). 2.0 ml fractions are collected from the outlet of the column, until all of the applied sample have eluted from the column. The collected fractions are analyzed for protein content (see above Protein concentration assay) and for protease activity by appropriate assays. An example of an appropriate assay is the Suc-AAPF-pNA assay (see Example 2B). Other appropriate assays are e.g., the CPU assay (se Example 1), and the Protazyme AK assay (see Example 2D). The conditions, e.g., pH, for the protease activity assays are adjusted to measure as many proteases in the fractionated sample as possible. The conditions of the assays referred to above are examples of suitable conditions. Other suitable conditions are mentioned above in the section dealing with measurement of protease activity. A protein peak with activity in one or more of the protease assays is defined as a protease peak. The purity of a protease peak is calculated as the protein amount in the peak divided with the total protein amount in all identified protease peaks.

The purity of a protease-containing enzyme product is calculated as the amount of protein in the acid-stable protease peak divided with the protein amount in all identified protease peaks using the above procedure.

The invention claimed is:

1. An animal feed composition comprising (a) at least one acid-stable subtilisin and (b) a vegetable protein or protein source, wherein the composition has a crude protein content of 50-800 g/kg, wherein the acid stability of the subtilisin means that the activity of the subtilisin in purified form, in a dilution corresponding to A280=1.0, is at least 40% of the reference activity of the subtilisin, wherein the activity of the subtilisin is measured after two hours incubation at a temperature of 37° C. in a buffer of 100 mM succinic acid, 100 mM HEPES, 100 mM CHES, 100 mM CABS, 1 mM CaCl2, 150 M KCl, and 0.01% Triton X-100 (pH 3.5), and wherein the reference activity is measured after two hours incubation at a temperature of 5° C. in the same buffer but adjusted to pH 9.0, wherein the activity and reference activity are measured after these incubations, at 25° C. in Suc AAPF pNA (pH 9.0).

2. The animal feed composition of claim 1, wherein the activity of the pure subtilisin is at least 45% of the reference activity of the subtilisin.

3. The animal feed composition of claim 2, wherein the activity of the subtilisin is at least 50% of the reference activity.

4. The animal feed composition of claim 3, wherein the activity of the subtilisin is at least 60% of the reference activity.

5. The animal feed composition of claim 1, wherein the subtilisin has a pH optimum in the range of 6.0-11.0.

6. The animal feed composition of claim 1, wherein the subtilisin is an *Acremonium chrysogenum*, ATCC 48272 subtilisin.

7. The animal feed composition of claim 1, wherein the subtilisin is an *Acremonium kiliense*, ATCC 20338 subtilisin.

8. The animal feed composition of claim 1, wherein the subtilisin is a *Bacillus* sp., NCIMB 40484 subtilisin.

9. The animal feed composition of claim 1, wherein the subtilisin is a *Bacillus alcalophilus*, NCIMB 10438 subtilisin.

10. The animal feed composition of claim 1, wherein the subtilisin is a *Fusarium oxysporum*, IFO 4471 subtilisin.

11. The animal feed composition of claim 1, wherein the subtilisin is a *Paecilomyces lilacinus*, CBS 102449 subtilisin.

12. The animal feed composition of claim 1, wherein the amount of the purified subtilisin corresponds to 0.01-200 mg subtilisin protein per kg feed.

13. The animal feed composition of claim 1, which further comprises at least one enzyme selected from the group consisting of galactanase, beta-glucanase, phytase, and xylanase.

14. The animal feed composition of claim 1, which further comprises one or more fat soluble vitamins and/or water soluble vitamins, and (c) one or more trace minerals.

* * * * *

UNITED STATES PATENT AND TRADEMARK OFFICE
CERTIFICATE OF CORRECTION

PATENT NO. : 7,608,444 B2
APPLICATION NO. : 11/074491
DATED : October 27, 2009
INVENTOR(S) : Oestergaard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 395 days.

Signed and Sealed this

Twelfth Day of October, 2010

David J. Kappos
*Director of the United States Patent and Trademark Office*

```
                       SEQUENCE LISTING

<160> NUMBER OF SEQ ID NOS: 7

<210> SEQ ID NO 1
<211> LENGTH: 27
<212> TYPE: PRT
<213> ORGANISM: Acremonium chrysogenum ATCC 48272

<400> SEQUENCE: 1

Ala Leu Val Thr Gln Asn Gly Ala Pro Trp Gly Leu Gly Thr Ile Ser
1               5                   10                  15

His Arg Gln Pro Gly Ser Thr Ser Tyr Ile Tyr
            20                  25

<210> SEQ ID NO 2
<211> LENGTH: 17
<212> TYPE: PRT
<213> ORGANISM: Bacillus alcalophilus NCIMB 10438

<400> SEQUENCE: 2

Asn Gln Val Thr Pro Trp Gly Ile Thr Arg Val Gln Ala Pro Thr Ala
1               5                   10                  15

Trp

<210> SEQ ID NO 3
<211> LENGTH: 17
<212> TYPE: PRT
<213> ORGANISM: Paecilomyces lilacinus CBS 102449

<400> SEQUENCE: 3

Ala Tyr Thr Gln Gln Pro Gly Ala Pro Trp Gly Leu Gly Arg Ile Ser
1               5                   10                  15

His
```

-continued

```
<210> SEQ ID NO 4
<211> LENGTH: 22
<212> TYPE: PRT
<213> ORGANISM: Fusarium oxysporum IFO 4471

<400> SEQUENCE: 4

Ala Leu Thr Thr Gln Ser Gly Ala Thr Trp Gly Leu Gly Thr Val Ser
1               5                   10                  15

His Arg Ser Arg Gly Ser
            20

<210> SEQ ID NO 5
<211> LENGTH: 397
<212> TYPE: PRT
<213> ORGANISM: Bacillus sp. NCIMB 40484
<220> FEATURE:
<221> NAME/KEY: SIGNAL
<222> LOCATION: (1)..(27)
<223> OTHER INFORMATION:
<220> FEATURE:
<221> NAME/KEY: PEPTIDE
<222> LOCATION: (118)..(397)
<223> OTHER INFORMATION:
<220> FEATURE:
<221> NAME/KEY: mat_peptide
<222> LOCATION: (28)..()
<223> OTHER INFORMATION:

<400> SEQUENCE: 5

Met Lys Phe Lys Lys Ile Ala Ala Leu Ser Leu Ala Thr Ser Leu Ala
        -25                 -20                 -15

Leu Phe Pro Ala Phe Gly Gly Ser Ser Leu Ala Lys Glu Ala Pro Lys
    -10                 -5                  -1  1               5

Pro Phe Gln Pro Ile Asn Lys Thr Leu Asp Lys Gly Ala Phe Glu Ser
                10                  15                  20

Gly Glu Val Ile Val Lys Phe Lys Asp Gly Val Ser Lys Lys Ala Gln
            25                  30                  35

Gly Ser Ala Leu Asn Lys Ala Glu Ala Asn Glu Gln Lys Ala Ser Ala
            40                  45                  50

Lys Asp Pro Phe Gln Val Leu Glu Val Ala Asp Val Asp Gln Ala Val
55                  60                  65

Lys Ala Leu Glu Asn Asn Pro Asn Val Glu Tyr Ala Glu Pro Asn Tyr
70                  75                  80                  85

Thr Phe Gln Ala Thr Trp Ser Pro Asn Asp Pro Tyr Tyr Ser Ala Tyr
                90                  95                  100

Gln Tyr Gly Pro Gln Asn Thr Ser Thr Pro Ala Ala Trp Asp Val Thr
            105                 110                 115

Arg Gly Ser Ser Thr Gln Thr Val Ala Val Leu Asp Ser Gly Val Asp
            120                 125                 130

Tyr Asn His Pro Asp Leu Ala Arg Lys Val Ile Lys Gly Tyr Asp Phe
            135                 140                 145

Ile Asp Arg Asp Asn Asn Pro Met Asp Leu Asn Gly His Gly Thr His
150                 155                 160                 165

Val Ala Gly Thr Val Ala Ala Asp Thr Asn Asn Gly Ile Gly Val Ala
                170                 175                 180

Gly Met Ala Pro Asp Thr Lys Ile Leu Ala Val Arg Val Leu Asp Ala
            185                 190                 195

Asn Gly Ser Gly Ser Leu Asp Ser Ile Ala Ser Gly Ile Arg Tyr Ala
            200                 205                 210
```

```
Ala Asp Gln Gly Ala Lys Val Leu Asn Leu Ser Leu Gly Cys Glu Cys
    215                 220                 225

Asn Ser Thr Thr Leu Lys Ser Ala Val Asp Tyr Ala Trp Asn Lys Gly
230                 235                 240                 245

Ala Val Val Val Ala Ala Gly Asn Asp Asn Val Ser Arg Thr Phe
            250                 255                 260

Gln Pro Ala Ser Tyr Pro Asn Ala Ile Ala Val Gly Ala Ile Asp Ser
            265                 270                 275

Asn Asp Arg Lys Ala Ser Phe Ser Asn Tyr Gly Thr Trp Val Asp Val
        280                 285                 290

Thr Ala Pro Gly Val Asn Ile Ala Ser Thr Val Pro Asn Asn Gly Tyr
    295                 300                 305

Ser Tyr Met Ser Gly Thr Ser Met Ala Ser Pro His Val Ala Gly Leu
310                 315                 320                 325

Ala Ala Leu Leu Ala Ser Gln Gly Lys Asn Asn Val Gln Ile Arg Gln
            330                 335                 340

Ala Ile Glu Gln Thr Ala Asp Lys Ile Ser Gly Thr Gly Thr Asn Phe
            345                 350                 355

Lys Tyr Gly Lys Ile Asn Ser Asn Lys Ala Val Arg Tyr
            360                 365                 370

<210> SEQ ID NO 6
<211> LENGTH: 367
<212> TYPE: PRT
<213> ORGANISM: Paecilomyces lilacinus CBS 143.75
<220> FEATURE:
<221> NAME/KEY: PEPTIDE
<222> LOCATION: (70)..(367)
<223> OTHER INFORMATION:
<220> FEATURE:
<221> NAME/KEY: PEPTIDE
<222> LOCATION: (84)..(367)
<223> OTHER INFORMATION:

<400> SEQUENCE: 6

Ala Arg Ala Pro Leu Leu Thr Pro Arg Gly Ala Ser Ser Ser Ser Thr
1               5                   10                  15

Ala Ser Thr Leu Ser Ser Ser Arg Thr Ala Cys Pro Ser Pro Leu Ser
            20                  25                  30

Thr Arg Leu Ser Ala Leu Cys Pro Arg Arg Pro Thr Ala Ser Thr Thr
        35                  40                  45

Thr Phe Ser Glu Ala Ser Arg Asn Leu Asn Ala Asn Asp Leu Lys Thr
    50                  55                  60

Leu Arg Asp His Pro Asp Val Glu Tyr Ile Glu Gln Asp Ala Ile Ile
65                  70                  75                  80

Thr Ile Asn Ala Tyr Thr Gln Gln Pro Gly Ala Pro Trp Gly Leu Gly
            85                  90                  95

Arg Ile Ser His Arg Ser Lys Gly Ser Thr Thr Tyr Glu Tyr Asp Thr
            100                 105                 110

Ser Gly Gly Ser Gly Thr Cys Ala Tyr Val Ile Asp Thr Gly Val Glu
        115                 120                 125

Ala Ser His Pro Glu Phe Glu Gly Arg Ala Ser Gln Ile Lys Ser Phe
    130                 135                 140

Ile Ser Gly Gln Asn Thr Asp Gly Asn Gly His Gly Thr His Cys Ala
145                 150                 155                 160

Gly Thr Ile Gly Ser Lys Thr Tyr Gly Val Ala Lys Lys Thr Lys Ile
            165                 170                 175
```

-continued

Tyr Gly Val Lys Val Leu Asp Asn Ser Gly Ser Gly Tyr Ser Gly
            180                 185                 190

Ile Ile Ser Gly Met Asp Phe Ala Val Gln Asp Ser Lys Ser Arg Ser
            195                 200                 205

Cys Pro Lys Gly Val Val Ala Asn Met Ser Leu Gly Gly Gly Lys Ala
        210                 215                 220

Gln Ser Val Asn Asp Gly Ala Ala Ala Met Ile Arg Ala Gly Val Phe
225                 230                 235                 240

Leu Ala Val Ala Ala Gly Asn Asp Asn Ala Asn Ala Ala Asn Tyr Ser
            245                 250                 255

Pro Ala Ser Glu Pro Thr Val Cys Thr Val Gly Ala Thr Thr Ser Ser
            260                 265                 270

Asp Ala Arg Ser Ser Phe Ser Asn Tyr Gly Asn Leu Val Asp Ile Phe
            275                 280                 285

Ala Pro Gly Ser Asn Ile Leu Ser Thr Trp Ile Gly Gly Thr Thr Asn
        290                 295                 300

Thr Ile Ser Gly Thr Ser Met Ala Thr Pro His Ile Val Gly Leu Gly
305                 310                 315                 320

Ala Tyr Leu Ala Gly Leu Glu Gly Phe Pro Gly Ala Gln Ala Leu Cys
            325                 330                 335

Lys Arg Ile Gln Thr Leu Ser Thr Lys Asn Val Leu Thr Gly Ile Pro
            340                 345                 350

Ser Gly Thr Val Asn Tyr Leu Ala Phe Asn Gly Asn Pro Ser Gly
            355                 360                 365

<210> SEQ ID NO 7
<211> LENGTH: 269
<212> TYPE: PRT
<213> ORGANISM: Bacillus sp. THS-1001

<400> SEQUENCE: 7

Asn Gln Val Thr Pro Trp Gly Ile Thr Arg Val Gln Ala Pro Thr Ala
1               5                   10                  15

Trp Thr Arg Gly Tyr Thr Gly Thr Gly Val Arg Val Ala Val Leu Asp
            20                  25                  30

Thr Gly Ile Ser Thr His Pro Asp Leu Asn Ile Arg Gly Gly Val Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Val
65                  70                  75                  80

Gly Val Ala Pro Asn Ala Glu Leu Tyr Ala Val Lys Val Leu Gly Ala
            85                  90                  95

Asn Gly Ser Gly Ser Val Ser Ser Ile Ala Gln Gly Leu Gln Trp Thr
            100                 105                 110

Ala Gln Asn Asn Ile His Val Ala Asn Leu Ser Leu Gly Ser Pro Val
        115                 120                 125

Gly Ser Gln Thr Leu Glu Leu Ala Val Asn Gln Ala Thr Asn Ala Gly
    130                 135                 140

Val Leu Val Val Ala Ala Thr Gly Asn Asn Gly Ser Gly Thr Val Ser
145                 150                 155                 160

Tyr Pro Ala Arg Tyr Ala Asn Ala Leu Ala Val Gly Ala Thr Asp Gln
            165                 170                 175

Asn Asn Asn Arg Ala Ser Phe Ser Gln Tyr Gly Thr Gly Leu Asn Ile
            180                 185                 190

```
                                -continued

Val Ala Pro Gly Val Gly Ile Gln Ser Thr Tyr Pro Gly Asn Arg Tyr
        195             200             205

Ala Ser Leu Ser Gly Thr Ser Met Ala Thr Pro His Val Ala Gly Val
        210             215             220

Ala Ala Leu Val Lys Gln Lys Asn Pro Ser Trp Ser Asn Thr Gln Ile
225             230             235                         240

Arg Gln His Leu Thr Ser Thr Ala Thr Ser Leu Gly Asn Ser Asn Gln
                245             250             255

Phe Gly Ser Gly Leu Val Asn Ala Glu Ala Ala Thr Arg
            260             265
```